(12) United States Patent
Ogawa et al.

(10) Patent No.: US 11,037,545 B2
(45) Date of Patent: Jun. 15, 2021

(54) INTERACTIVE PERSONAL ASSISTIVE DEVICES AND SYSTEMS WITH ARTIFICIAL INTELLIGENCE, AND RELATED METHODS

(71) Applicant: FACET LABS, LLC, Los Gatos, CA (US)

(72) Inventors: Stuart Ogawa, Los Gatos, CA (US); Lindsay Sparks, Seattle, WA (US); Koichi Nishimura, San Jose, CA (US); Wilfred P. So, Mississauga (CA); Jane Chen, Los Gatos, CA (US)

(73) Assignee: FACET LABS, LLC, Los Gatos, CA (US)

( * ) Notice: Subject to any disclaimer, the term of this patent is extended or adjusted under 35 U.S.C. 154(b) by 0 days.

(21) Appl. No.: 16/982,642

(22) PCT Filed: Mar. 19, 2019

(86) PCT No.: PCT/US2019/022929
§ 371 (c)(1),
(2) Date: Sep. 21, 2020

(87) PCT Pub. No.: WO2019/183062
PCT Pub. Date: Sep. 26, 2019

(65) Prior Publication Data
US 2021/0027759 A1 Jan. 28, 2021

Related U.S. Application Data

(60) Provisional application No. 62/644,747, filed on Mar. 19, 2018.

(51) Int. Cl.
*G10L 15/26* (2006.01)
*G10L 13/02* (2013.01)
*G16Y 40/30* (2020.01)
*G06F 40/58* (2020.01)
*G10L 15/28* (2013.01)
*H04L 29/08* (2006.01)

(52) U.S. Cl.
CPC ............. *G10L 13/02* (2013.01); *G06F 40/58* (2020.01); *G10L 15/26* (2013.01); *G10L 15/28* (2013.01); *G16Y 40/30* (2020.01); *H04L 67/20* (2013.01)

(58) Field of Classification Search
CPC ......... A61B 5/165; A61B 5/168; G10L 25/66; G10L 25/69; G10L 15/26
See application file for complete search history.

(56) References Cited

U.S. PATENT DOCUMENTS

| | | | |
|---|---|---|---|
| 9,747,902 B2* | 8/2017 | Jasinschi | G10L 25/66 |
| 10,657,960 B2* | 5/2020 | Tokunaga | G06F 16/3329 |
| 2015/0081299 A1* | 3/2015 | Jasinschi | G10L 25/66 |
| | | | 704/246 |
| 2019/0244608 A1* | 8/2019 | Choi | G10L 15/30 |
| 2020/0245013 A1* | 7/2020 | Weerasinghe | H04N 21/6547 |

* cited by examiner

*Primary Examiner* — Daniel Abebe

(57) ABSTRACT

A smart and scalable dementia assistant device is provided that converses with a patient in voices familiar with the patient. It utilizes content learned from the patient and content provided by family, friends, caregivers, and doctors, and autonomously adjusts conversations based on the changing state of the patient's dementia state. The device autonomously controls IoT devices (e.g. doors, elevators, tvs, medical dispensers) to help and assist the dementia patient using oral and IoT sensors.

26 Claims, 29 Drawing Sheets

INTERACTIVE PERSONAL ASSISTIVE DEVICES AND SYSTEMS WITH ARTIFICIAL INTELLIGENCE, AND RELATED METHODS

CROSS-REFERENCE TO RELATED APPLICATIONS

This application claims priority to U.S. Provisional Patent Application No. 62/644,747 filed on Mar. 19, 2018 and titled "Interactive Dementia Assistive Devices and Systems with Artificial Intelligence, and Related Methods", the entire contents of which are herein incorporated by reference.

This application also incorporates by reference the entire contents of the following patent application:

U.S. Provisional Patent Application No. 62/543,777 filed on Aug. 10, 2017 and titled "ORAL COMMUNICATION DEVICE AND COMPUTING ARCHITECTURE FOR PROCESSING DATA AND OUTPUTTING USER FEEDBACK, AND RELATED METHODS".

TECHNICAL FIELD

The following generally relates to interactive dementia assistive devices and related computing architectures and methods for processing data and outputting user feedback, such as via audio or visual media, or both.

DESCRIPTION OF THE RELATED ART

Dementia afflicts 50 million people in the world and 10 million new cases arise each year. The dementia rate is doubling every 20 years reaching 75 million in 2030 and 131.5 million in 2050.

The National Institute on Aging conducted a study in 2010 estimating the annual cost to help dementia patients was $215 billion a year to care for dementia patients, surpassing heart disease ($102 billion) and cancer ($77 billion).

In some cases, it costs $7,000 to $12,000/month for around the clock dementia care. This cost precludes many families from being able to afford dedicated dementia care, and as a result families and relatives are typically relied upon to help loved ones. The toll and impact on family members taking care of dementia patients can break families apart and, at a minimum, causes severe anger and frustration among family members and friends.

In many cities, there are long waiting lists (e.g. many months long) to receive care from a memory care facility. The cost and availability of dedicated memory care units will continue to worsen as the aging baby boomer demographic rises. Globally, these same problems are occurring as noted in the first link above.

It is recognized that a patient's dementia state can vary over the course of a week, or even within day. This unpredictable patient behavior devastates caregivers through fatigue, energy loss, and anger. For example, a more passive, relaxed and engaging patient state could occur in the morning and regress to an agitated or fearful state in the afternoon. On a different day, the same patient could function normally, from a memory perspective throughout the morning and early afternoon, and then begin forgetting in the late afternoon, also known as "sundowner" syndrome. In either case, it is exhausting and challenging for a family members and care givers to long term communicate and support the loved one as the dementia changes throughout the day, day to day, week-to-week, etc.

It will be appreciated that "dementia" is an overall term for a set of symptoms that are caused by disorders affecting the brain. Symptoms may include memory loss and difficulties with thinking, problem-solving or language, severe enough to reduce a person's ability to perform everyday activities. A person with dementia may also experience changes in mood or behavior.

Dementia is progressive, which means the symptoms will gradually get worse as more brain cells become damaged and eventually die.

Dementia is not a specific disease. Many diseases can cause dementia, including Alzheimer's disease, vascular dementia (due to strokes), Lewy Body disease, head trauma, fronto-temporal dementia, Creutzfeldt-Jakob disease, Parkinson's disease, and Huntington's disease. These conditions can have similar and overlapping symptoms.

Mobile devices (e.g. cell phones, smart phones), wearable devices (e.g. smart watches), and on-body devices (e.g. trackers worn around the neck or embedded in clothing) have been used to help track persons with dementia and to provide audio reminders or text reminders. However, it is herein recognized that existing technologies are often too complex to use, especially when a person from dementia is suffering from cognitive lapse. These technologies also are perceived to be a threatening presence of constant surveillance, as these technologies are considered foreign to persons with dementia. These technologies are also considered to be restrictive in movement and behavior, since the person with dementia will need to carry or wear an electronic device, or otherwise maintain the electronic device in some other fashion.

It is also herein recognized that existing technologies that attempt to be responsive to a person with dementia are too simplistic. A single response, or a limited set of responses, are used to react to a detected event of a person with dementia. Examples of responses include beeps, buzzes, flashing lights, text reminders, and pre-recorded voice messages. It is herein recognized that these approaches can be ineffective to help a person with dementia. Furthermore, these approaches are intended to "blanket" all persons with dementia, but is inappropriate since there are many different symptoms and levels of dementia, which vary over time (even within a day). In effect, these technologies can reduce or degrade the dignity of persons with dementia.

It is further herein recognized that dementia assistive devices that have more complex response functionalities, are typically slower and have delayed outputs to the person with dementia.

These difficulties apply to other assistive devices used to assist people with aging challenges and cognitive/mental disorders.

These, and other technical challenges, lead to limited adoption of dementia assistive devices, assistive devices for the aging population, and assistive devices for those with cognitive/mental disorders.

BRIEF DESCRIPTION OF THE DRAWINGS

Embodiments will now be described by way of example only with reference to the appended drawings wherein.

DETAILED DESCRIPTION

Figure 1:
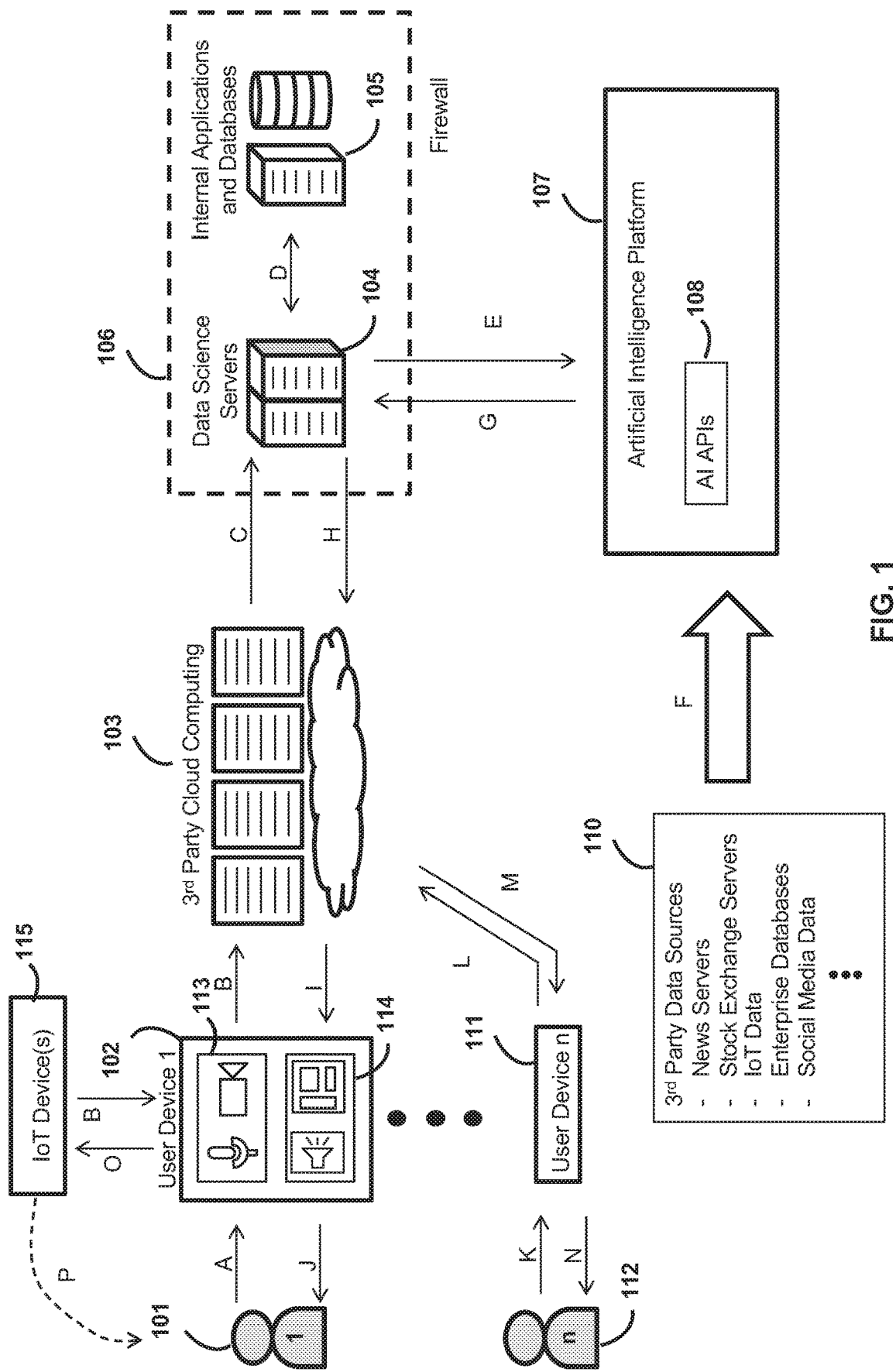
FIG. 1 is a schematic diagram of an example computing architecture for ingesting user data via user devices, and providing big data computations and machine learning using a data enablement platform.

It will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures and components have not been described in detail so as not to obscure the example embodiments described herein. Also, the description is not to be considered as limiting the scope of the example embodiments described herein.

It is herein recognized that there is a strong desire for a personalized and cost effective solution to assist people with varying degrees of dementia. This help includes specifically helping and assisting the dementia patient with day to day living activities and social interactions as well as helping, assisting, monitoring, and taking medical actions by family, relatives, caregivers, doctors, and other health care providers.

In an example embodiment, the system described herein includes Artificial Intelligence (AI) computations residing on a cloud computing system and on one or more smart devices. The system machine learns a given patient's questions, behaviors, activity patterns, fond memories, preferences, vital signs, etc. throughout the day and that dynamically outputs data to the patient. In an example aspect, the data is personalized to the patient. The data, for example, is one or more of: visual data, audio data, a physical action, a physical stimulation to the person, an electrical stimulation to the person, a chemical stimulation to the person, etc. In another example aspect, the data is being outputted in response to something the patient does (e.g. has said, has gestured, has expressed through their facial expression, has actioned with their body, etc.). In an example aspect, these outputted responses include voices (i.e. audio data) that are familiar with to the patient (e.g. voices of a spouse, family member, friend, doctor, health care provider, etc.). In another example aspect, the system or device(s), or both, autonomously increase and decrease the level of patient assistance (e.g. interactions, projected memory recall images/videos/slideshows, and IoT controlled devices) with the goal to assist the dementia patient and exercise their brain while not putting the patient in danger. In another example aspect, the system or device(s), or both, machine learns and autonomously makes recommendations to family members, friends, care givers, doctors, and health care professionals surfacing new patient dementia trends and making recommendations to help the loved one given their patient history. In another example aspect, the system or device(s), or both, machine learns new patient interactions (e.g. questions, statements, facial expressions, body postures, gestures, actions, etc.) not previously made by the patient and the workflow routes these patient interactions to an appropriate person. A responder (e.g. the appropriate person) helps to generate a response to the new interaction via their computing device, and their response in turn is sent to the cloud system and the patient's device(s). In another example aspect, when the same new interaction arises again, the system or device(s), or both, outputs the same response to the patient using the information previously provided by the responder.

While many of the examples described herein relate to people with dementia, the systems, devices and processes described herein can also be used to help people with aging challenges, cognitive challenges, and mental disorders.

The interactions between the patient and the personalized smart device(s) include day-to-day suggestions, activity reminders, doctor's appointments, family gatherings etc. Forms of these interactions include, for example, monitoring one or more of: verbal interaction, audio interaction without words (e.g. moaning, yelling, slurring, etc.), subvocalizations, hand gestures (e.g. including and not limited to sign language), body posture, eye movement, location of a person, actions of a person, brain signals, muscle signals, nerve signals, body temperature, heart rate signals, blood pressure, etc.

In an example embodiment, smart device(s) (ex. personal assistant devices, smartphone/table) and smart cloud ecosystem(s) interact with the dementia patient throughout the entire day. The device-to-patient interactions include using photographs, pictures, video, and audio data (e.g. music, environmental sounds, voices, etc.) that would engage the patient. For example, a video of familiar people (e.g. family or friends) can be outputted to the patient. In another example embodiment, the interactions include life-like synthesized voices of actual family members, friends, care givers, doctors, and other health care providers) so that the patient experiences a conversation as if he or she is really talking with a person over the phone. For example, sample utterances of a patient's family member are turned into a synthesized voice and outputted via a voice synthesizer digital signal processing (DSP).

Verbal interactions, for example, can include frequently asked questions asked by the patient to family members and doctors. Alternatively, an ad hoc conversation initiated by the daughter's synthesized voice, on the smart device, could ask mom to talk about a fun family trip they took 10 years ago. This level of smart device conversation with recognized voices calms the loved one and provides the sense of security that loved one's, in person, cannot provide around the clock. Many times these questions occur after midnight till 6 AM.

These aforementioned interactions are primarily through human to machine conversations, but the device(s) could also include monitoring the person's vital signs, brain waves, physical GPS movement, etc. and incorporate this sensor data in order to augment and enhance responses provided from the system and device(s) to the patient.

This AI based system can help provide mental and physical stretch tests and goals so that doctors, health care providers, and family members can track the loved one's progress over time and the system. With the collective oral responses and patient monitoring IoT data, the system can make data science driven recommendations to doctors, care givers, family members, such as increasing walking time and performing less sedentary activity events, such as watching too much television. Another example is recommending adult coloring books in order to improve eye, hand, and brain fine motor skills. Other autonomous and personalized IoT smart device and system actions include recognizing who I am and unlocking IoT doors, ad hoc playing my favorite jazz music, reminding me to take my prescriptions, telling me my activities for the day, reading my favorite mystery thriller audio book, etc. that I might not be able to do on his/her own because he/she is has "sundowner" characteristics at the moment.

In an example embodiment, an oral communication user device (e.g. a device that includes a microphone) records oral information from a user (e.g. the user's word and sounds) to interact with a data enablement system. A data enablement system processes the voice data to extract, at least the words and of the spoken language, and accordingly processes the data using artificial intelligence computing software and data science algorithms. The data obtained from the oral communication device is processed in combination with, or comparison with, or both, internal data specific to an organization (e.g. a given family or social network, a healthcare organization, a company, etc.) and external data (e.g. available from data sources outside a given organization). The computing architecture ingests data from external data sources and internal data sources to provide real-time outputs or near real-time data outputs, or both. The data outputs are presented to the user as audio feedback, or visual feedback, or both. Other types of user feedback may be used, including tactile feedback, physical feedback, chemical feedback, brain-signal feedback, muscle-signal feedback, nerve-signal feedback, etc. Other machine actions may be initiated or executed based on the data outputs.

These devices that interact with a person with dementia are also herein called a user device, an oral communication device, an edge device, a smart device, smart edge device, edge node, smart edge node, and intelligent edge node. The functionalities and form of these devices vary. For example, in various embodiments and examples, functionalities and forms of these devices include one or more of: devices being worn; devices implanted into body; devices that are surface attached to body; human-computing interface devices, including brain-computing interfaces; and devices that are positioned in living areas where dementia patients live, walk, move and interact.

It will also be appreciated that persons with dementia are also herein referred to as patients.

In an example embodiment, the devices, systems and the methods described herein provide persons with dementia and their caregivers and support community with more intelligent, timely, and predictable assistance in the caring of persons with dementia.

Turning to FIG. 1, a user device 102 interacts with a user 101. The user device 102 includes, amongst other things, input devices 113 and output devices 114. The input devices include, for example, one or more microphones and one or more cameras. The output devices include, for example, one or more of: an audio speaker, a multimedia projector, a holographic display device, a display screen, a tactile feedback device, a robotic mechanism, a chemical dispensing device, etc. Non-limiting examples of user devices include a mobile phone, a smart phone, a tablet, a desktop computer, a laptop, an e-book, an in-car computer interface, wearable devices, implanted devices, brain-computer interfaces, human-computer interfaces (e.g. that track one or more of brain signals, nerve signals, muscle signals, etc.), a robot, a prosthetic device, an ambulatory device, augmented reality devices, and virtual reality devices. The user device is in communication with a $3^{rd}$ party cloud computing service 103, which typically includes banks of server machines. Multiple user devices 111 (e.g. also called a smart device, an oral communication device, an intelligent edge node, an edge device, an intelligent edge device, etc.), which correspond to multiple users 112, can communicate with the $3^{rd}$ part cloud computing service 103.

The cloud computing service 103 is in data communication with one or more data science server machines 104. These one or more data science server machines are in communication with internal application and databases 105, which can reside on separate server machines, or, in another example embodiment, on the data science server machines. In an example embodiment, the data science computations executed by the data science servers and the internal applications and the internal databases are considered proprietary to given organization, and therefore are protected by a firewall 106. Currently known firewall hardware and software systems, as well as future known firewall systems can be used.

In an alternative example, the data science servers 104 and the databases 105 are not protected by a firewall.

The data science server machines, also called data science servers, 104 are in communication with an artificial intelligence (AI) platform 107. The AI platform 107 includes one or more AI application programming interfaces (APIs) 108. As will be discussed later, the AI platform runs different types of machine learning algorithms suited for different functions, and these algorithms can be utilized and accessed by the data science servers 104 via an AI API.

The AI platform also is connected to various data sources 110, which may be $3^{rd}$ party data sources or internal data sources, or both. Non-limiting examples of these various data sources include: news servers, stock exchange servers, IoT data, enterprise databases, social media data, etc.

In an example embodiment, the network of the servers 103, 104, 105, 107 and optionally 110 make up a data enablement system. The data enablement system provides relevant to data to the user devices, amongst other things. In an example embodiment, all of the servers 103, 104, 105 and 107 reside on cloud servers.

An example of operations is provided with respect to FIG. 1, using the alphabetic references. At operation A, the user device 102 receives input from the user 101. For example, the user is speaking and the user device records the audio data (e.g. voice data) from the user. The user could be recording or memorializing thoughts to himself or herself, or providing himself or herself a to-do list to complete in the future, or providing a command or a query to the data enablement system. In an example aspect, a data enablement application is activated on the user device and this application is placed into a certain mode, either by the user or autonomously according to certain conditions.

At operation B, the user device transmits the recorded audio data to the $3^{rd}$ party cloud computing servers 103. In an example embodiment, the user device also transmits other data to the servers 103, such as contextual data (e.g. time that the message was recorded, information about the user, data from surrounding IoT devices, the mode of the data enablement application during which the message was recorded, etc.). For example, IoT devices 115 include wearable devices (e.g. hear rate monitor, step counter), home monitoring devices, smart door mechanisms, smart toilet mechanisms, car monitoring devices, etc. These servers 103 apply machine intelligence, including artificial intelligence, to extract data features from the audio data and, if available, the contextual data. These data features include, amongst other things: text, sentiment, emotion, background noise, a command or query, or metadata regarding the storage or usage, or both, of the recorded data, or combinations thereof.

In an example embodiment, either in operation A or operation B, a new interaction (e.g. new question, new statement, new gesture, new facial expression, new physical action, new body state, etc.) that has been detected by the user device or by the servers is marked as being new. This new interaction, and any related response, is then stored in memory so that, when the interaction is detected again, the same or similar response is outputted. In an example aspect, if the new interaction is detected a certain number of times within a certain time frame, then the new interaction and the related response is marked as a frequent interaction in memory.

At operation C, the servers 103 send the extracted data features and the contextual data to the data science servers 104. In an example embodiment, the servers 103 also send the original recorded audio data to the data science servers 104 for additional processing.

At operation D, the data science servers 104 interact with the internal applications and databases 105 to process the received data. In particular, the data science servers store and executed one or more various data science algorithms to process the received data (from operation C), which may include processing data and algorithms obtained from the internal applications and the databases 105.

In alternative, or in addition to operation D, the data science servers 104 interact with the AI platform 107 at operations E and G. In an example embodiment, the data science servers 104 have algorithms that process the received data, and these algorithms transmit information to the AI platform for processing (e.g. operation E). The information transmitted to the AI platform can include: a portion or all of the data received by the data science servers at operation C; data obtained from internal applications and databases at operation D; results obtained by the data science servers from processing the received data at operation C, or processing the received data at operation D, or both; or a combination thereof. In turn, the AI platform 107 processes the data received at operation E, which includes processing the information ingested from various data sources 110 at operation F. Subsequently, the AI platform 107 returns the results of its AI processing to the data science servers in operation G.

Based on the results received by the data science servers 104 at operation G, the data science servers 104, for example, updates its internal applications and databases 105 (operation D) or its own memory and data science algorithms, or both. The data science servers 104 also provide an output of information to the $3^{rd}$ party cloud computing servers 104 at operation H. This outputted information may be a direct reply to a query initiated by the user at operation A. In another example, either in alternative or in addition, this outputted information may include ancillary information that is either intentionally or unintentionally requested based on the received audio information at operation A. In another example, either in alternative or in addition, this outputted information includes one or more commands that are either intentionally or unintentionally initiated by received audio information at operation A. These one or more commands, for example, affect the operation or the function of the user device 102, or other user devices 111, or IoT devices 115, or a combination thereof.

The $3^{rd}$ party cloud computing servers 104, for example, takes the data received at operation H and applies transformation to the data, so that the transformed data is suitable for output at the user device 102. For example, the servers 104 receive text data at operation H, and then the servers 104 transform the text data to spoken audio data. This spoken audio data is transmitted to the user device 102 at operation I, and the user device 102 then plays or outputs the audio data to the user at operation J.

In an example embodiment, at operation O, Response data from the user device 102 or originating from the server 104 is used initiate an action of the IoT devices 115. In some examples, at operation P, an action of the IoT device 115 affects the user 101. For example, if the user 101 says "I have fallen", as detected by the microphone on the user device 102, or if the user device 102 detects that the user device has fallen via image processing of images obtained by the camera, then the user device 102 will initiate a smart door locking mechanism (i.e. an IoT device) to automatically unlock so as to allow paramedics or a caregiver to access the person. Alternatively, the user device 102 is a wearable device that includes an accelerometer, and this accelerometer detects that the person has fallen.

This process is repeated for various other users 112 and their user devices 111. For example, another user speaks into another user device at operation K, and this audio data is passed into the data enablement platform at operation L. The audio data is processed, and audio response data is received by the another user device at operation M. This audio response data is played or outputted by the another user device at operation N.

In another example embodiment, the user uses touchscreen gestures, augmented reality gestures or movements, virtual reality gestures or movements, typing, etc. to provide inputs into the user device 102 at operation A, either in addition or in alternative to the oral input. In another example embodiment, the user device 102 provides visual information (e.g. text, video, pictures) either in addition or in alternative to the audio feedback at operation J.

It is also appreciated that that the user device 102 is also equipped with onboard intelligent hardware capabilities (e.g. memory and processors) that can locally execute data science computations and AI computations. In other words, there are data science and AI computations that are executed locally on the user device 102 without contact the data enablement platform. In an example aspect, the data enablement platform sends updated data science and AI computations to the user device 102, so that the user device 102 can better perform local computations.

Figure 2A:
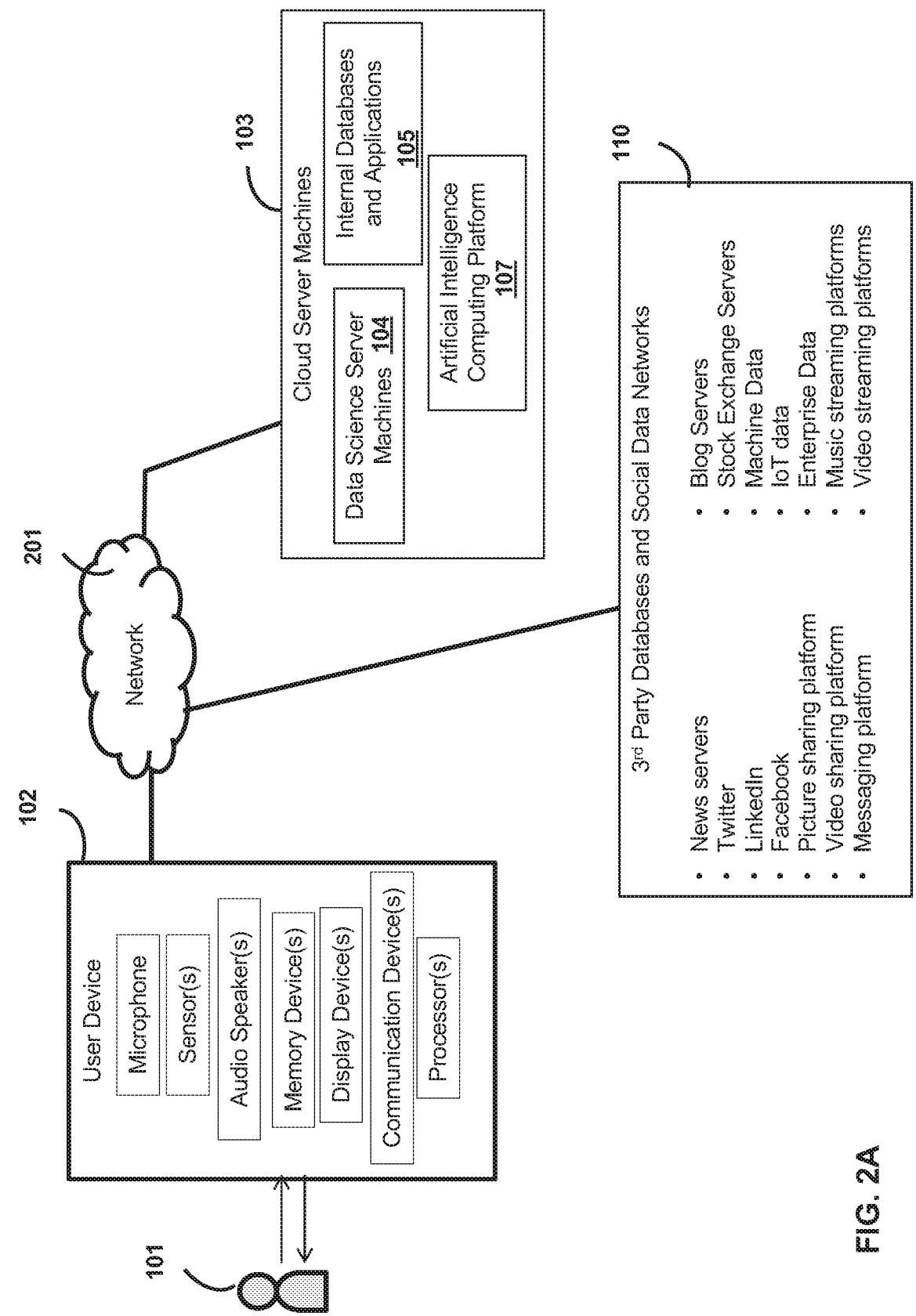
FIGS. 2A and 2B are other schematic diagrams of other example representations of the computing architecture in FIG. 1.

Turning to FIG. 2A, another example of the servers and the devices are shown in a different data networking configuration. The user device 102, the cloud computing servers 103, the data science servers 104, AI computing platform 107, and the various data sources 110 are able to transmit and receive data via a network 201, such as the Internet. In FIG. the data science computations, internal databases and applications and the AI computations are implemented on cloud server machines 103. For example, the cloud server machines are provided by one cloud service provider, or are provided by different cloud service providers.

Figure 2B:
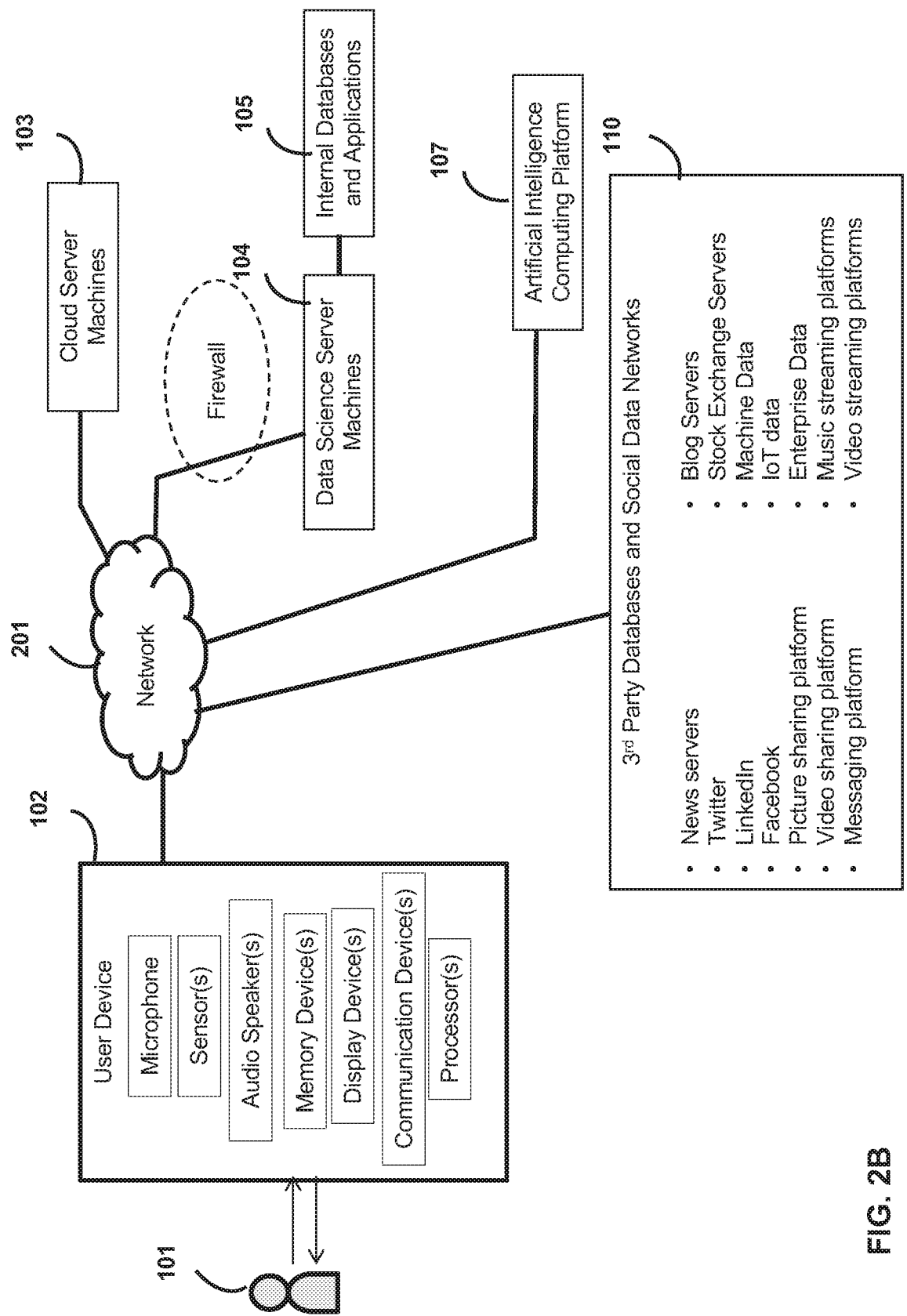

In another example embodiment in FIG. 2B, the data science servers 104 and the internal applications and databases 105 are in communication with each other over a private network for enhanced data security. In another example embodiment, the servers 104 and the internal applications and the databases 105 are in communication with each other over the same network 201.

As shown in FIGS. 2A and 2B, example components of the user device 102 include one or more microphones, one or more other sensors (e.g. cameras, infrared sensors, motion detection sensors, etc.), audio speakers, one or more memory devices, one or more display devices, a communication device, and one or more processors. The memory devices include, for example, RAM and ROM. The processors, for example, include one or more of: single core processors, multi-core processors, graphic processing units (GPUs), tensor processing units (TPUs), and neuromorphic chips. In an example embodiment, the one or more processors include a quantum processor, which can be used for various applications, including for executing data encryption and decryption computations to protect the user's data.

In an example embodiment, the user device's memory includes various "bots" that are part of the data enable application, which can also reside on the user device. In an example aspect, the one or more bots are considered chat bots or electronic agents. These bots include processing that also resides on the $3^{rd}$ party cloud computing servers 103. Examples of chat bot technologies that can be modified or integrated (or both) into the system described herein include, but are not limited to, the trade names Siri, Google Assistant, Alexa, and Cortana. In an example aspect, the bot used herein has various language dictionaries that are focused on various topics (e.g. including, but not limited to, common family topics of a given person with dementia, common daily activities of a given person with dementia, common healthcare terms relevant to a person with dementia, etc.). In an example aspect, the bot used herein is configured to understand questions and answers specific to these various topics. In another example aspect, a bot used herein translates language interactions from a first language to a second language.

In an example aspect, the bot used herein learns the unique voice of the user, which the bot consequently uses to learn behavior that may be specific to the user. This anticipated behavior in turn is used by the data enablement system to anticipate future questions and answers related to a given topic. This identified behavior is also used, for example, to make action recommendations to help the user achieve a result, and these action recommendations are based on the identified behaviors (e.g. identified via machine learning) of successful users in the same industry. In an example application, the questions and answers are for a given person with dementia, and the recommendations and the behaviors relate helping a caregiver respond to and assist the given person with dementia.

In an example aspect, the bot applies machine learning to identify unique data features in the user voice. Machine learning can include, deep learning. Currently known and future known algorithms for extracting voice features are applicable to the principles described herein. Non-limiting examples of voice data features, also herein called audio voice attributes, include one or more of: tone, frequency (e.g. also called timbre), loudness, rate at which a word or phrase is said (e.g. also called tempo), phonetic pronunciation, lexicon (e.g. choice of words), syntax (e.g. choice of sentence structure), articulation (e.g. clarity of pronounciation), rhythm (e.g. patterns of long and short syllables), melody (e.g. ups and downs in voice), vowel duration, peak vocal sound pressure (e.g. measured in SPL), continuity of phonation, tremor, pitch variability, and loudness variability. As noted above, these data features or audio voice attributes can be used to identify behaviors and meanings of the user, and to predict the content, behavior and meaning of the user in the future. It will be appreciated that prediction operations in machine learning include computing data values that represent certain predicted features (e.g. related to content, behavior, meaning, action, etc.) with corresponding likelihood values. Other types of interactions about the patient are tracked and learned over time, including one or more of: routines, locations, activities of daily living, facial expressions, body postures, body temperature, blood pressure, heart rate, brain signals, muscle signals, nerve signals, eye movements, etc.

The user device may additionally or alternatively receive video data or image data, or both, from the user, and transmit this data via a bot to the data enablement platform. The data enablement platform is therefore configured to apply different types of machine learning to extract data features from different types of received data. For example, the $3^{rd}$ party cloud computing servers use natural language processing (NLP) algorithms or deep neural networks, or both, to process voice and text data. In another example, the $3^{rd}$ party cloud computing servers use machine vision, or deep neural networks, or both, to process video and image data. As noted above, these computations can also occur locally on the user device.

Figure 3:
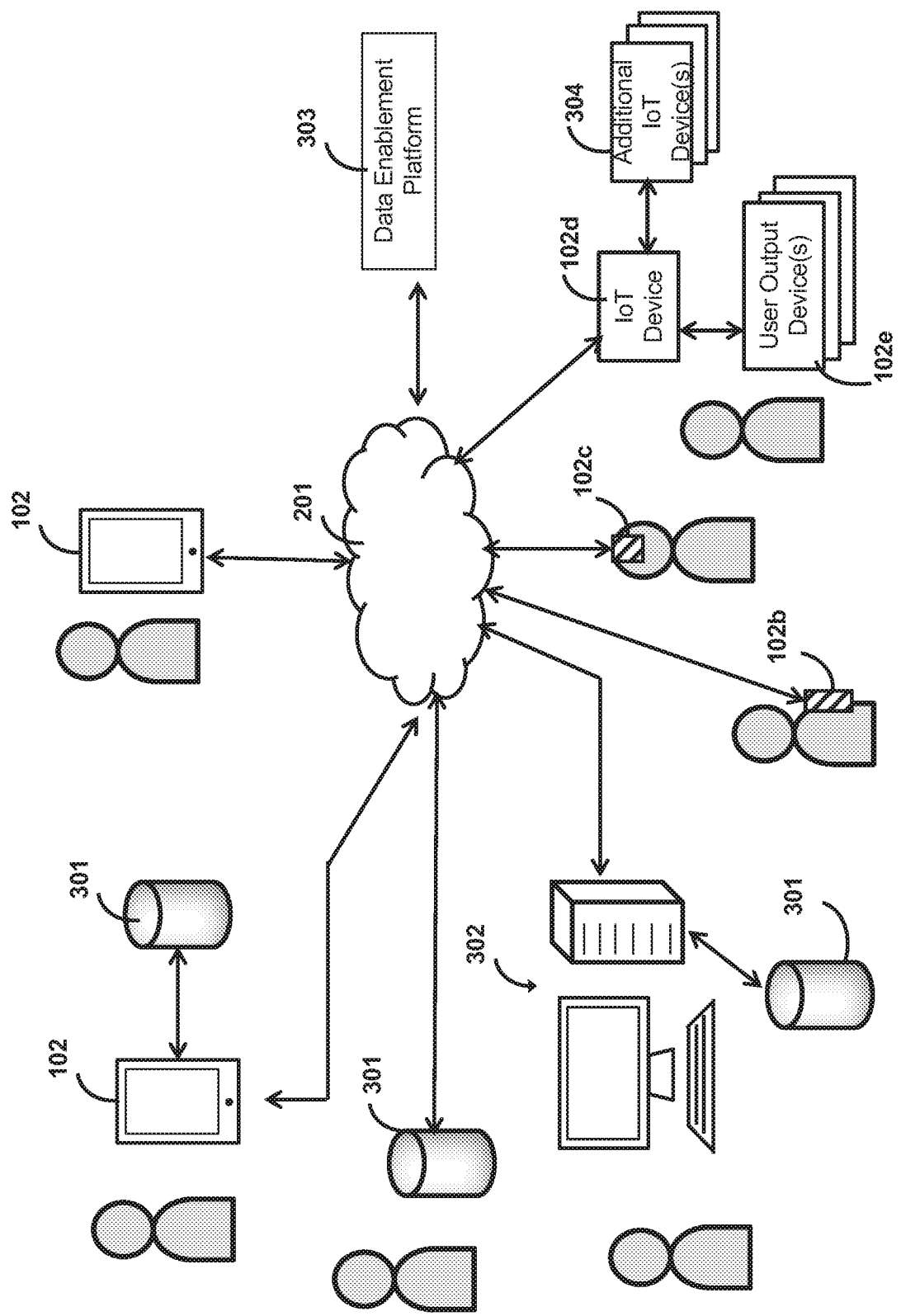
FIG. 3 is a schematic diagram of oral communication devices (OCDs) in communication with respective user devices, which are in turn in communication with the data enablement platform.

Turning to FIG. 3, an example embodiment of an oral communication device (OCD) 301 is shown, which operates in combination with the user device 102 to reduce the amount of computing resources (e.g. hardware and processing resources) that are consumed by the user device 102 to execute the data enablement functions, as described herein. In some cases, the OCD 301 provides better or additional sensors than a user device 102. In some cases, the OCD 301 is equipped with better or additional output devices compared to the user device 102. In an example embodiment, the OCD includes one or more microphones, one or more cameras, one or more audio speakers, and one or more multimedia projects which can project light onto a surface. The OCD also includes processing devices and memory that can process the sensed data (e.g. voice data, video data, etc.) and process data that has been outputted by the data enablement platform 303. As noted above, the data enablement platform 303 includes, for example, the servers 103, 104, 105, and 107.

As shown in FIG. 3, the OCD 301 is in data communication with the user device via a wireless or wired data link. In an example embodiment, the user device 102 and the OCD 301 are in data communication using a Bluetooth protocol. The user device 102 is in data communication with the network 201, which is in turn in communication with the data enablement platform 303. In operation, when a user speaks or takes video, the OCD 301 records the audio data or visual data, or both. The OCD 301, for example, also pre-processes the recorded data, for example, to extract data features. The pre-processing of the recorded data may include, either in addition or in the alternative, data compression. This processed data or the original data, or both, are transmitted to the user device 102, and the user device transmits this data to the data enablement platform 303, via the network 201. The user device 102 may also transmit contextual data along with the data obtained or produced by the OCD 301. This contextual data can be generated by the data enablement application running on the user device 102, or by the OCD 301.

Outputs from the data enablement platform 303 are sent to the user device 102, which then may or may not transmit the outputs to the OCD 301. For example, certain visual data can be displayed directly on the display screen of the user device 102. In another example embodiment, the OCD receives the inputs from the user device and provides the user feedback (e.g. plays audio data via the speakers, displays visual data via built-in display screens or built-in media projectors, etc.).

In an example embodiment, the OCD 301 is in data connection with the user device 102, and the OCT 301 itself has a direct connection to the network 201 to communicate with the data enablement platform 303.

Similar functionality is applicable to the other instance of the OCD 301 that is in data communication with the desktop computer 302. In particular, it is herein recognized that many existing computing devices and user devices are not equipped with sensors of sufficient quality, nor with processing hardware equipped to efficiently and effectively extract the features from the sensed data. Therefore, the OCD 301 supplements and augments the hardware and processing capabilities of these computing devices and user devices.

In another example, the OCD 301 is the user device 102 itself. In other words, no additional mobile device or computing device is required other than the OCD. The OCD 301 is equipped with the components of the user device 102, as specified herein. A user device 102 interacts directly with the OCD 301, and the OCD 301 interacts directly with the network 201 to communicate with the data enablement platform 303.

In another example, a user just uses the user device 102.

In another example, the user device is a wearable 102b (e.g. worn or attached to a part of the user's body). In another example, the user device is an implanted device 102c that interacts with a part of the user's body.

In a more general example, the data enablement platform interacts with an IoT device 102d, which then communicates data to one or more user output devices 102e. In another example aspect, the IoT device 102d interacts with one or more additional IoT devices 304 that may not directly interact with the user.

Figure 4:
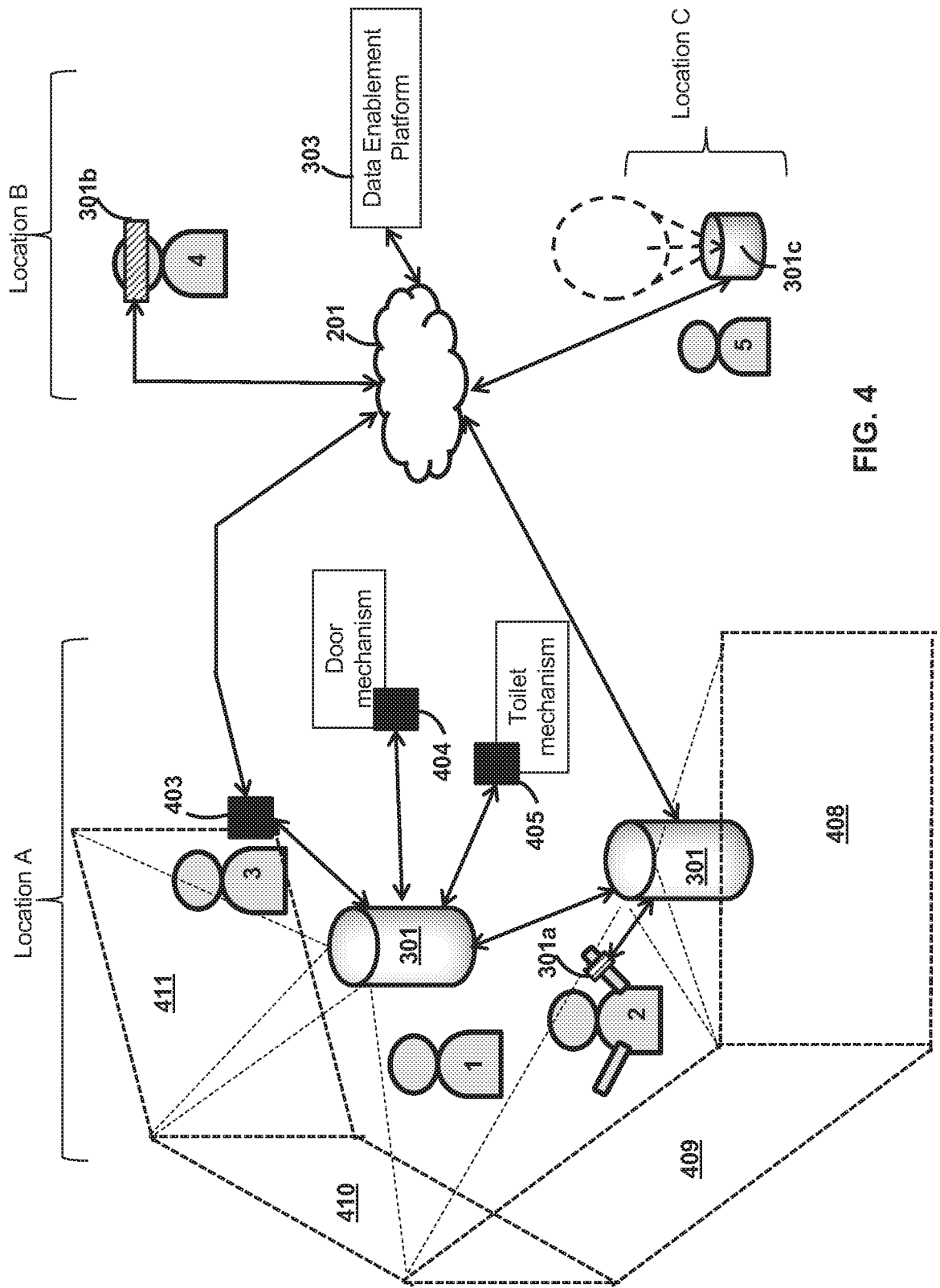
FIG. 4 is a schematic diagram showing different embodiments of an OCD, including wearable devices, an OCD embodiment configured to provide augmented reality or virtual reality, and a holographic projector.

Turning to FIG. 4, an OCD 301 is shown being used in at a given location (Location A). Various users 1, 2 and 3 are shown in this example, but it will be appreciated that a single person can interact with a single OCD 301.

The OCD 301 can be used to record data (e.g. audio data, visual data, etc.) and provide data to people (e.g. persons with dementia) who may or may not have any additional devices. The OCD records the oral conversation of one or more persons to, for example, take notes. In another example, the OCD engages in conversation with one or more of these persons (e.g. users 1, 2, 3). In another aspect, the OCD also links to the user devices to give them information, for example, in real-time about the topics being discussed during a conversation. For example, user 1 is a person with dementia and does not prefer to use any additional device beyond their OCD(s) 301. User 2 is another person with dementia that wears another type of OCD 301a (e.g. a smart watch, or some other type of wearable device) that is in wireless data communication with an OCD 301. User 3 is a visitor (e.g. a caregiver, a family member, etc.) that is visiting user 1 and user 2 and has their own mobile device 403, which is data communication with an OCD. At location A, the OCD 301 communicates with other IoT devices that can help user 1 and user 2, and also adapt to user 3 who does not have dementia.

For example, a smart door mechanism 404 is an IoT device in data communication with the OCD 301. The door mechanism 404 is configured to actuate any one or more of: locking the door, unlocking the door, opening the door, and closing the door. The door mechanism can perform an actuation in response to receiving a command or some other type of data from the OCD 301.

In another example, a smart toilet mechanism 405 is an IoT device in data communication with the OCD 301. The toilet mechanism 404 is configured to actuate any one or more of: flushing, raising the toilet seat, and lowering the toilet seat. The toilet mechanism can perform an actuation in response to receiving a command or some other type of data from the OCD 301.

The OCD also reduces the computing resources (e.g. hardware and processing resources) on the individual user devices (e.g. devices 403 and 301a).

In an example embodiment, the devices 403, 404, 405 and 301a are in data communication with the OCD 301 via a wireless connection (while in other examples, they communicate via a wired connection). In an example embodiment, some of these devices do not have Internet access, but other devices do have Internet access over separate data connections. Therefore, the OCD 301 uses one or more of these data connections to transmit and receive data from the data enablement platform 303. For example, an OCD communicates with a mobile device 403 to access the network 201. In another example, there are two OCDs that are in communication with each other; a first one of the OCDs has direct access to the network 201, and the second one of the OCDs accesses the network 201 via the first one of the OCDs.

The OCD may use different communication routes based on the available bandwidth, which may be dictated by the user devices.

The data obtained by the OCD, either originating from a user device or the data enablement platform, can be distributed amongst the devices (e.g. devices 403, 301*a*, 404, 405, etc.) that are in communication with the OCD. The OCD can also provide central user feedback (e.g. audio data, visual data, etc.) to the users (e.g. user 1, user 2, or user 3, or a combination thereof) in the immediate vicinity.

It will be appreciated that the OCD therefore acts as a local central input and output device. In another example aspect, the OCD also acts as a local central processing device to process the sensed data, or processed the data from the data enablement platform, or both. In another example aspect, OCD also acts as a local central communication hub.

In an example embodiment, the OCD, either in the alternative or in addition, the OCD has its own network communication device and transmits and receives data, via the network 201, with the data enablement platform 303.

The OCD provides various functions in combination with the data enablement platform 303. In an example operation, the OCD provides an audio output that orally communicates actions to be done by a person. In an example operation, the OCD records the discussion items that are spoken by a person, and automatically creates text containing a summary of the conversation. In an example operation, the OCD monitors the flow of a person talking and the current time, and at appropriate times (e.g. pauses, hard stops, end of sentences, etc.) interjects to provide feedback (e.g. audio, visual, physical, tactile, etc. feedback) to move on to another topic. In this way, if a person with dementia is focused too much on a first topic that is not appropriate or beneficial (e.g. circular and repeated discussion about a first topic), then the OCD interjects at an appropriate time to help the person think about a second topic. For example, the second topic is something that is considered very safe and familiar to the user. In another example, the second topic is something that helps the person to calm down.

In an example operation, the OCD monitors topics and concepts being discussed and, in real-time, distributes ancillary and related data intelligence to other devices (e.g. IoT devices, other mobile devices, other devices of contacts located in other locations). In an example operation, the OCD monitors topics and concepts being discussed and, in real-time, determines if pertinent related news or facts are to be shared and, if so, interjects the conversation by providing audio or visual output that provides the pertinent related news, media content, or facts. For example, people with dementia "live in the past". In other words, they may believe that the present day is sometime in past (e.g. 1950s, 1960s, 1970s, 1980s, etc.). Based on the interaction with the OCD, for example, it is determined that the person believes it is a first earlier time period (e.g. 1950s) and the OCD outputs media content relevant to the 1950s. Later on, the OCD detects that the same person believes it is a second earlier time period (e.g. 1970s) and the OCD outputs media content that is relevant to the 1970s. The media content can also be specific to interests, people and location that are familiar to the person with dementia. In a more general example embodiment, the OCD outputs media content that is relevant to the perceived reality of the person with dementia, as detected by the person's interaction and historical information.

In another example operation, the OCD monitors topics and concepts being discussed and, in real-time, determines if a user provided incorrect information and, if so, interjects the conversation by providing audio or visual output that provides the correct information. In another example operation, the OCD provides different feedback to different user devices, to suit the interests and goals specific the different users, during the meeting. In another example operation, the OCD uses cameras and microphones to record data to determine the emotion and sentiment of various users, which helps to inform decision making. In another example embodiment, the OCD includes one or more media projectors to project light images on surrounding surfaces.

It will be appreciated that while the housing body of the OCD is shown to be cylindrical, in other example embodiments, it has different shapes.

Continuing with FIG. 4, the users (e.g. user 1, user 2, user 3) in Location A are interacting with one or more OCDs, and a user (e.g. user 4) in a separate location (i.e. Location B) is interacting with another OCD. Together, these users, although at different locations can interact with each through digital voice and imagery data. The data enablement platform processes their data inputs, which can include voice data, image data, physical gestures and physical movements. These data inputs are then used to by the data enablement platform to provide feedback to the users.

At Location A, two OCD units 301 are in data communication with each other and project light image areas 411, 410, 409, 408. These projected light image areas are positioned in a continuous fashion to provide, in effect, a single large projected light image area that can surround or arc around the users. This produces an augmented reality or virtual reality room. For example, one OCD unit projects light image areas 411 and 410, and another OCD unit projects light image areas 409 and 408. In an example embodiment, users can interact with the augmented reality images.

User 2 is wearing another embodiment of an OCD 301*a*. This embodiment of the OCD 301*a* includes a microphone, audio speakers, a processor, a communication device, and other electronic devices to track gestures and movement of the user. For example, these electronic devices include one or more of a gyroscope, an accelerometer, and a magnetometer. In an example embodiment, the OCD 301*a* is trackable using triangulation computed from radio energy signals from the two OCD units 301 positioned at different locations (but both within Location A).

The users at Location A can talk and see the user at Location B.

Conversely, the user at Location B is wearing a virtual reality or augmented reality headset, which is another embodiment of an OCD 301*b*, and uses this to talk and see the users at Location A. The OCD embodiment 301*b* projects or displays images near the user's eyes, or onto the user's eyes. The OCD embodiment 301*b* also includes a microphone, audio speaker, processor, and communication device, amongst other electronic components. Using the OCD embodiment 301*b*, the user is able to see the same images being projected onto one or more of the image areas 411, 410, 409, and 408.

Similarly, at Location C, user 5 interacts with an OCD 301*c*, which displays holographic images. The OCD 301*c* can be used to interact with other users at other locations, or can be used to display media content, or can be used to display synthesized personal content (e.g. a synthesized holographic image or video or a person familiar to user 5).

Figure 5:
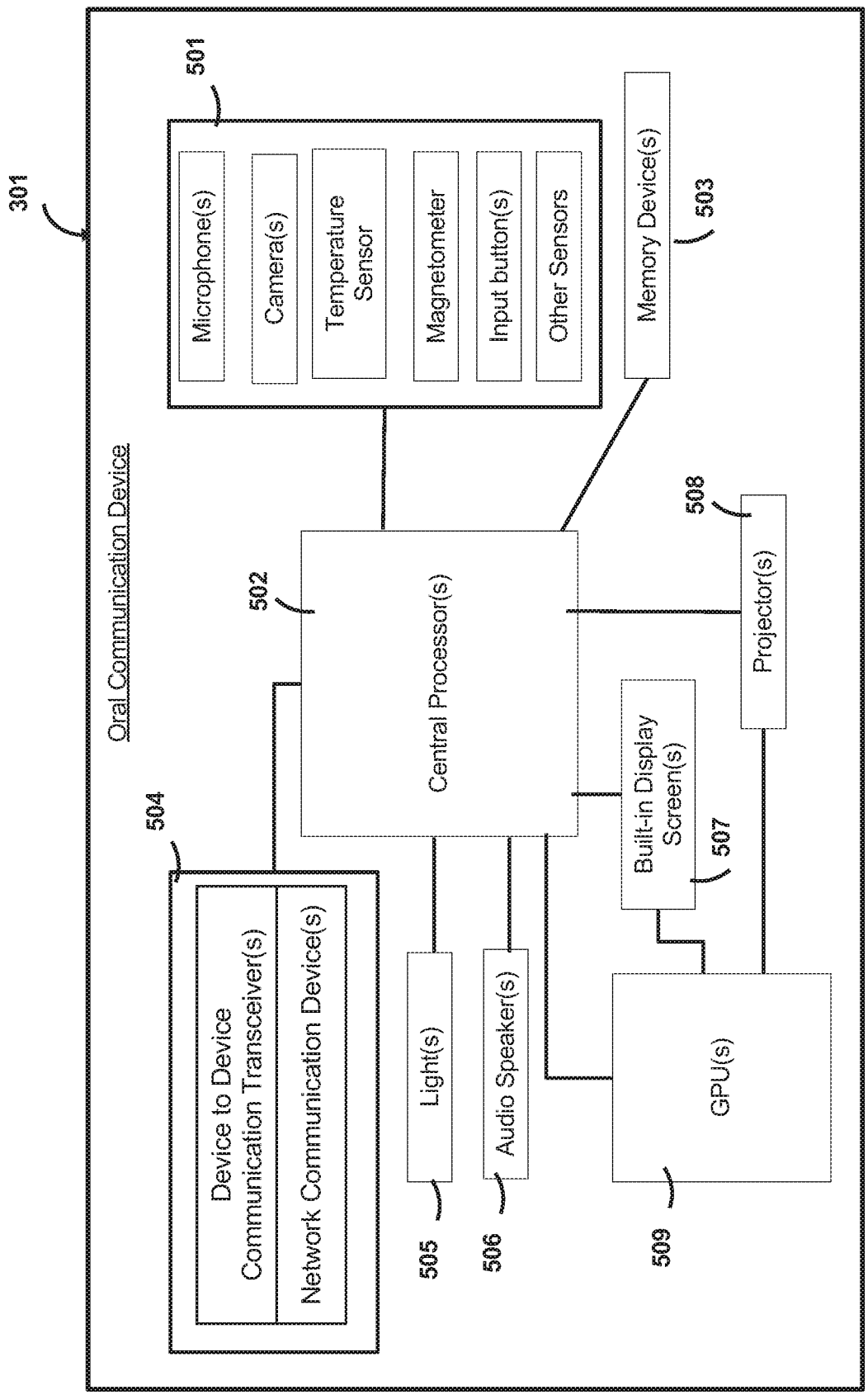
FIG. 5 is a block diagram showing example components of the OCD.

Turning to FIG. 5, example components that are housed within the OCD 301 are shown. The components include one or more central processors 502 that exchange data with various other devices, such as sensors 501. The sensors include, for example, one or more microphones, one or more cameras, a temperature sensor, a magnetometer, one or more input buttons, and other sensors. The one or more processors 502 include one or more of: central processing units, ASICs (application specific integrated circuits), DSP chips (digital signal processing chips), FPGAs (field programmable gate arrays), GPUs (graphic processing units), TPUs (tensor processing units), and neuromorphic chips. Other currently known and future known processors can be used in the OCD.

In an example embodiment, there are multiple microphones that are oriented to face in different directions from each other. In this way, the relative direction or relative position of an audio source can be determined. In another example embodiment, there are multiple microphones that are tuned or set to record audio waves at different frequency ranges (e.g. a microphone for a first frequency range, a microphone for a second frequency range, a microphone for a third frequency range, etc.). In this way, more definition of audio data can be recorded across a larger frequency range.

In an example embodiment, there are multiple cameras that are oriented to face in different directions. In this way, the OCD can obtain a 360 degree visual field of view. In another example, one or more cameras have a first field of a view with a first resolution and one or more cameras have a second field of view with a second resolution, where the first field of view is larger than the second field of view and the first resolution is lower than the second resolution. In a further example aspect, the one or more cameras with the second field of view and the second resolution can be mechanically oriented (e.g. pitched, yawed, etc.) while the one or more cameras with the first field of view and the first resolution are fixed. In this way, video and images can be simultaneously taken from a larger perspective (e.g. the surrounding area, people's bodies and their body gestures), and higher resolution video and images can be simultaneously taken for certain areas (e.g. people faces and their facial expressions).

The OCD also includes one or more memory devices 503, lights 505, one or more audio speakers 506, one or more communication devices 504, one or more built-in-display screens 507, and one or more projectors 508 (e.g. media projector, holographic display, etc.). The OCD also includes one or more GPUs 509. GPUs or other types of multi-threaded processors are configured for executing AI computations, such as neural network computations. The GPUs are also used, for example, to process graphics that are outputted by the projector(s) or the display screen(s), or both.

In an example embodiment, the communication devices include one or more device-to-device communication transceivers, which can be used to communicate with one or more user devices. For example, the OCD includes a Bluetooth transceiver. In another example aspect, the communication devices include one or more network communication devices that are configured to communicate with the network 201, such as a network card or WiFi transceiver, or both.

In an example embodiment, there are multiple audio speakers 506 positioned on the OCD to face in different directions. In an example embodiment, there are multiple audio speakers that are configured to play sound at different frequency ranges.

In an example embodiment, the built-in display screen forms a curved surface around the OCD housing body. In an example embodiment, there are multiple media projectors that project light in different directions.

In an example embodiment, the OCD is able to locally pre-process voice data, video data, image data, and other data using on-board hardware and machine learning algorithms. This reduces the amount of data being transmitted to the data enablement platform 303, which reduced bandwidth consumption. This also reduces the amount of processing required by the data enablement platform.

Figure 6:
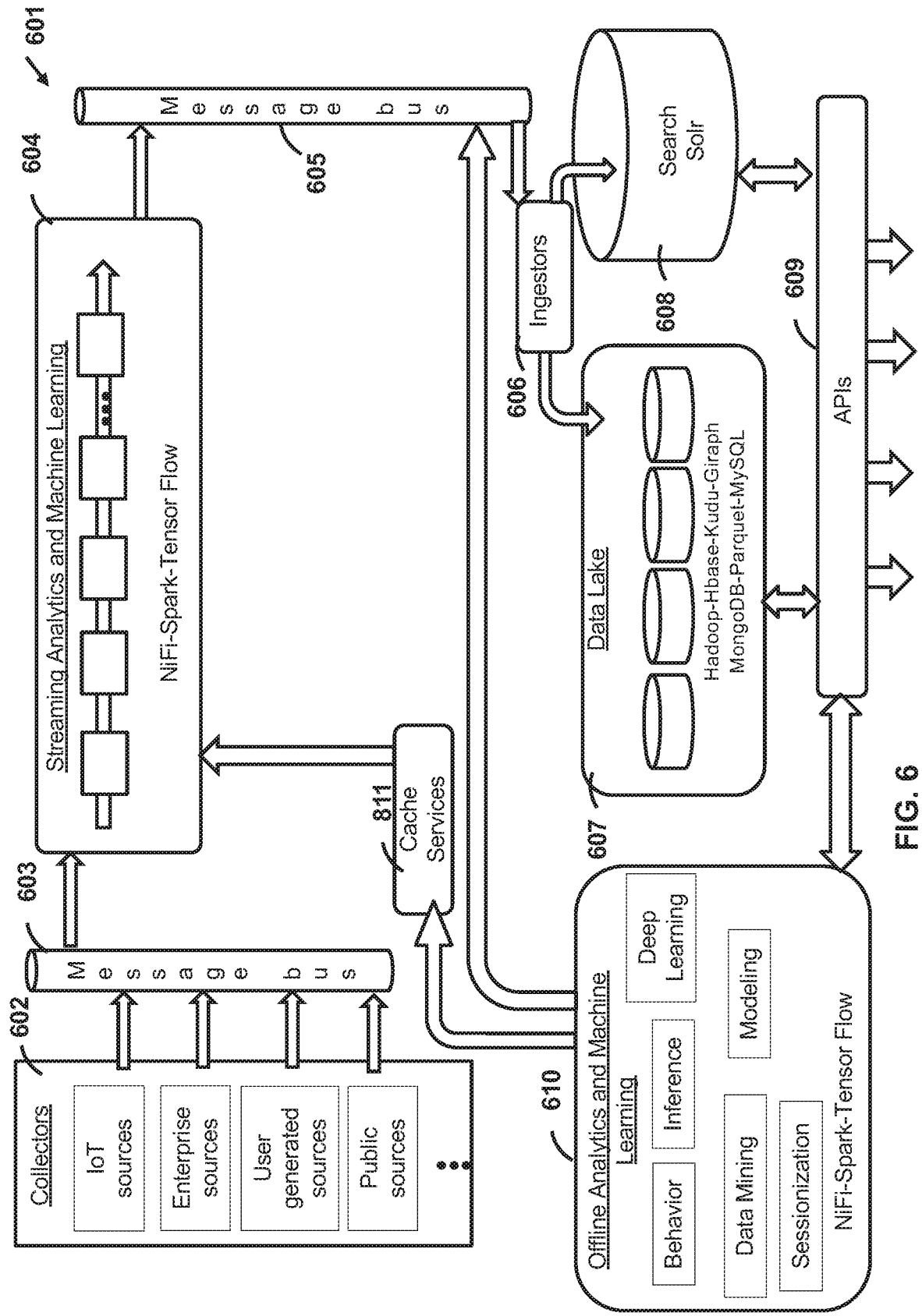
FIG. 6 is a schematic diagram showing an example computing architecture for an artificial intelligence (AI) platform, which is part of the data enablement platform.
Figure 7:
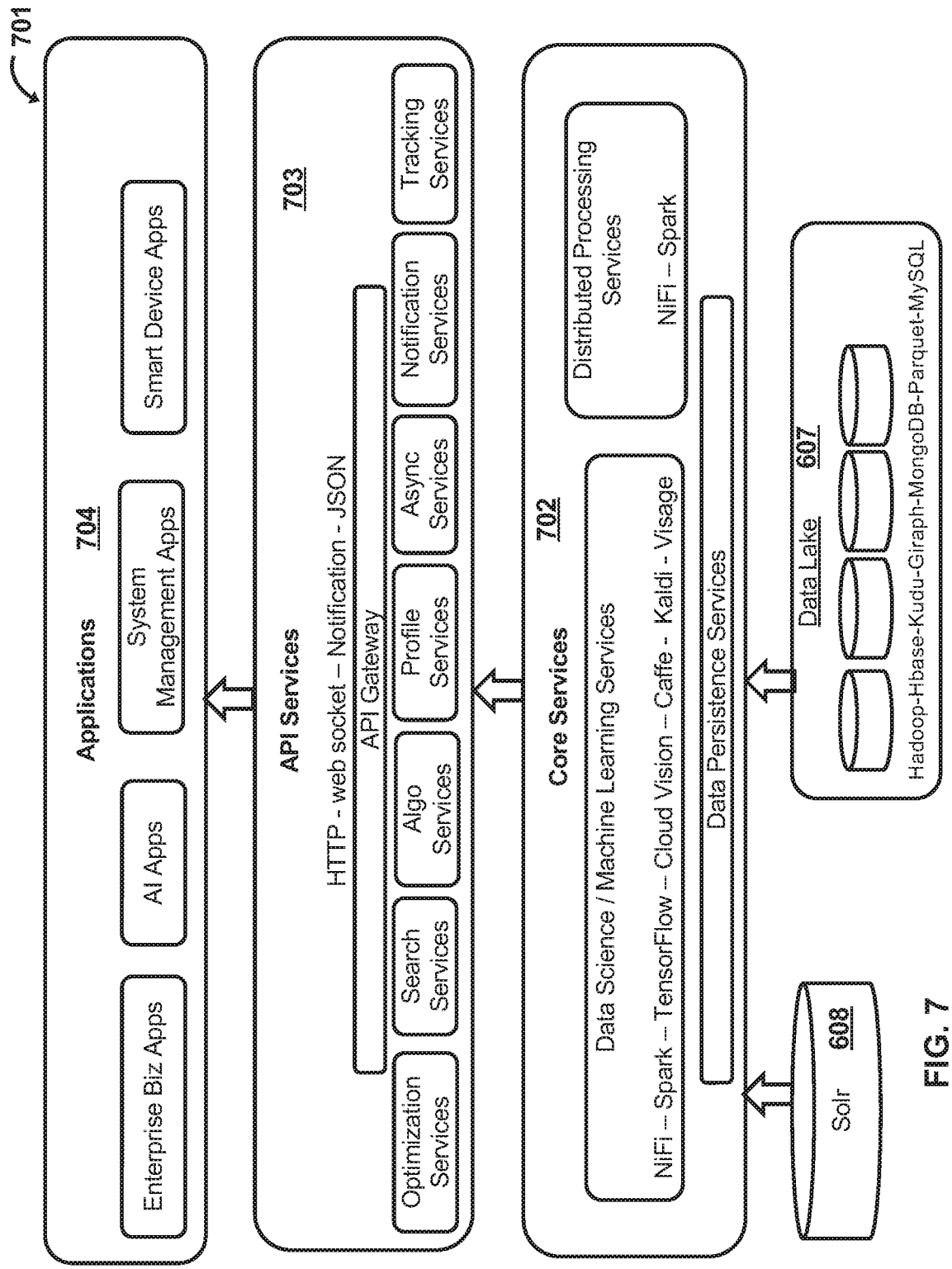
FIG. 7 is a schematic diagram showing another example aspect of the computing architecture for the AI platform.

FIGS. 6 and 7 show example computing architectures of the data enablement platform, which are in alternative to the above-discussed architectures. In another example, these computing architectures shown in FIGS. 6 and 7 are incorporated into the above-discussed architectures.

Turning to FIG. 6, an example computing architecture 601 is provided for collecting data and performing machine learning on the same. This architecture 601, for example, is utilized in the AI platform 107.

The architecture 601 includes one or more data collector modules 602 that obtain data from various sources, such as IoT devices, enterprise software, user generated websites and data networks, and public websites and data networks. Non-limiting examples of IoT devices include sensors placed within a home, car, hospital or city. IoT devices can also be used to determine the status of users (e.g. wearable devices). Enterprise software can include CRM software and healthcare software. User generated data includes social data networks, messaging applications, blogs, online photo websites and databases, online video websites and databases, and online forums. Public websites and data networks include government websites and databases, banking organization websites and databases, insurance websites and databases, hospital websites and databases. Other examples of public sources include websites that provide streaming video of other locations (e.g. beach front scenery, a countryside scenery, city environments, home environments, etc.). It can be appreciated that other digital data sources may be collected by the data collector modules. Other examples of public sources include music streaming services.

The collected data is transmitted via a message bus 603 to a streaming analytics engine 604, which applies various data transforms and machine learning algorithms. For example, the streaming analytics engine 604 modules to transform the incoming data, apply language detection, add custom tags to the incoming data, detect trends, and extract objects and meaning from images and video. It will be appreciated that other modules may be incorporated into the engine 604. In an example implementation, the engine 604 is structured using one or more of the following big data computing approaches: NiFi, Spark and TensorFlow. It will be appreciated that other currently-known and future known big data computing approaches can be used according the principles described herein.

NiFi automates and manages the flow of data between systems. More particularly, it is a real-time integrated data logistics platform that manages the flow of data from any source to any location. NiFi is data source agnostic and supports different and distributes sources of different formats, schemas, protocols, speeds and sizes. In an example implementation, NiFi operates within a Java Virtual Machine architecture and includes a flow controller, NiFi extensions, a content repository, a flowfile repository, and a provenance repository.

Spark, also called Apache Spark, is a cluster computing framework for big data. One of the features of Spark is Spark Streaming, which performs streaming analytics. It ingests data in mini batches and performs resilient distributed dataset (RDD) transformations on these mini batches of data.

TensorFlow is software library for machine intelligence developed by Google. It uses neural networks which operate on multiple central processing units (CPUs), GPUs and TPUs.

Offline analytics and machine learning modules 610 are also provided to ingest larger volumes of data that have been gathered over a longer period of time (e.g. from the data lake 607). These modules 610 include one or more of a behavior module, an inference module, a sessionization module, a modeling module, a data mining module, and a deep learning module. These modules can also, for example, be implemented by NiFi, Spark or TensorFlow, or combinations thereof. Unlike these the modules in the streaming analytics engine 604, the analysis done by the modules 610 is not streaming. The results are stored in memory (e.g. cache services 611), which then transmitted to the streaming analytics engine 604.

The resulting analytics, understanding data and prediction data, which are outputted by the streaming analytics engine 604, are transmitted to ingestors 606, via the message bus 605. The outputted data from the offline analytics and machine learning modules 610 can also be transmitted to the ingestors 606.

The ingestors 606 organize and store the data into the data lake 607, which comprise massive database frameworks. Non-limiting examples of these database frameworks include Hadoop, HBase, Kudu, Giraph, MongoDB, Parquet and MySQL. The database could also be a decentralized database, including and not limited to the Interplanetary File System (IPFS). The data outputted from the ingestors 606 may also be inputted into a search platform 608. A non-limiting example of the search platform 608 is the Solr search platform built on Apache Lucene. The Solr search platform, for example, provides distributed indexing, load balanced querying, and automated failover and recovery.

Data from the data lake and the search engine are accessible by API services 609.

Turning to FIG. 7, another architecture 701 is shown, which is used after the data has been stored in the data lake 607 and indexed into the search platform 608.

A core services module 702 obtains data from the search platform 608 and the data lake 607 and applies data science and machine learning services, distributed processing services, data persistence services to the obtained data. For example, the data science and machine learning services are implemented using one or more of the following technologies: NiFi, Spark, TensorFlow, Cloud Vision, Caffe, Kaldi, and Visage. It will be appreciated that other currently known and future known data science or machine learning platforms can be used to execute algorithms to process the data. Non-limiting examples of distributed processing services include NiFi and Spark.

The API services module 703 includes various APIs that interact with the core services module 702 and the applications 704. The API services module 703, for example, exchanges data with the applications in one or more of the following protocols: HTTP, Web Socket, Notification, and JSON. It will be appreciated that other currently known or future known data protocols can be used.

The module 703 includes an API gateway, which accesses various API service modules. These API service modules are also denoted as the APIs 609 in FIG. 6. Non-limiting examples of API service modules include an optimization services module, a search services module, an algorithm services module, a profile services module, an asynchronous services module, a notification services module, and a tracking services module. Other examples of API service modules include messaging service modules, media service modules, conversation bot service modules, and activity bot service modules.

In an example embodiment, the modules 703 and 702 are part of the AI platform 107, and the applications 704 reside on one or more of the data science servers 104, the internal applications and databases 105, and the user device 102. Non-limiting examples of the applications include enterprise business applications, AI applications, system management applications, and smart device applications.

Figure 8A:
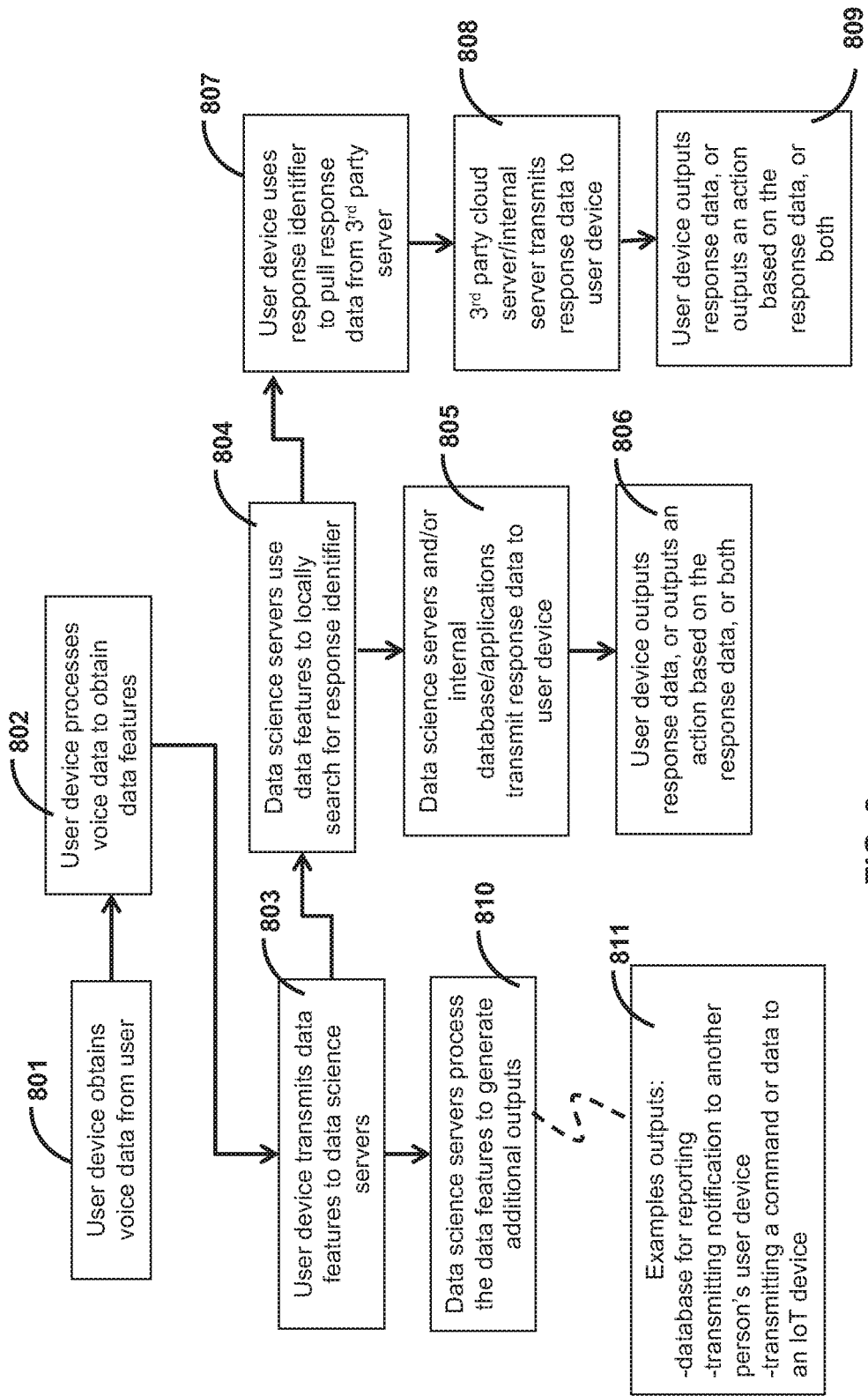
FIGS. 8a, 8b and 8c are flow diagrams of example executable instructions for processing voice data obtained from a user device.

Turning to FIG. 8*a*, an example embodiment is shown for a voice-based interaction. It will be appreciated that other types of interactions can be used, and that the data science would be used to understand those other types of interactions.

Block 801: User device obtains voice data from user.

Block 802: User device processes voice data to obtain data features. For example, the data features are text obtained from the voice data using speech-to-text computations.

Block 803: User device transmits data features to data science servers.

Block 804: Data science servers use data features to locally search for response identifier. For example, the data science servers include a listing of response identifiers associated with stored text (e.g. questions, utterances, etc.). If a sufficient match is found between the obtained data features (e.g. the text obtained from the voice data) and the stored text, then the corresponding response identifier is identified as a search result. In an example aspect, the sufficient match is based on a percentage value. A response identifier, for example, is a pointer to a data location of a response. In another example embodiment, the response identifier is a uniform resource locator (URL).

Block 805: Data science servers and/or internal database/ applications transmit response data to user device.

Block 806: User device outputs response data, or outputs an action based on the response data, or both.

Block 807: Following block 804, the data science server sends the response identifier to the user device. The user device then uses the response identifier to pull response data from 3rd party server.

Block 808: 3rd party cloud server/internal server transmits the response data to user device.

Block 809: User device outputs response data, or outputs an action based on the response data, or both.

Block 810: Following block 803, the data science servers process the data features to generate additional outputs. Examples (block 811) of these additional outputs include one or more of: populating a database for reporting; transmitting a notification to another person's user device (e.g. a caregiver, a family member, a doctor, etc.); and transmitting a command or data to an IoT device.

In an example embodiment at block 810, after the data science server has detected that the patient has said a phrase or question a certain number of times within a certain time frame (e.g. 4 times within a day, 2 times within an hour, etc.), then the data science server sends a notification (e.g. message, email, text message, phone call, etc.) to another person's user device telling them to take action (e.g. contact the patient). In another example, the notification includes a communication link (e.g. phone number, video conference, audio conference, etc.) between the other person and the patient.

In an example embodiment, the operations in blocks 805 and 806 occur after block 804, but not the operations 807-809. In an alternative embodiment, the operations in blocks 807, 808 and 809 occur after block 804, but not the operations 805-806.

Figure 8B:
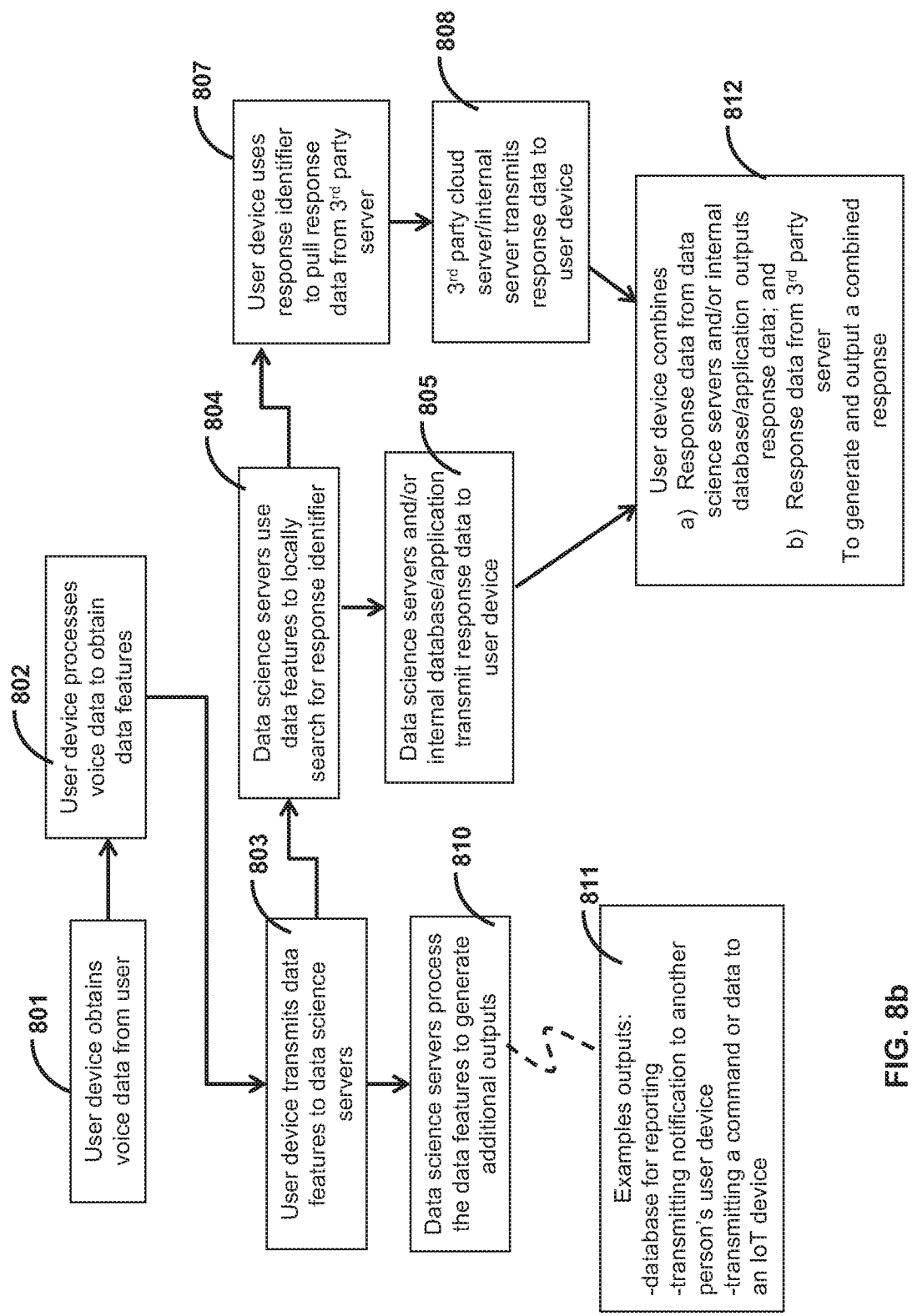

FIG. 8b shows another example embodiment that is similar to FIG. 8a. In FIG. 8b, the response data from the data science servers (or the internal database/applications) and the response data from a $3^{rd}$ party server is combined to generate a combined response at the user device (block 812). For example, the data obtained at block 805 is a familiar person's voice (e.g. a family member's voice) that is combined with a $3^{rd}$ party visual data (e.g. a video or images). The familiar person's voice data is, for example, a prelude introducing the visual data. For example, the combined response is: a familiar person's voice data that plays (e.g. "Hi Mom, look at these pictures of where we grew up.") followed by the visual data (e.g. a video of the place where the family grew up). In another example, the voice data of the familiar person is a postlude, or is a voice-over combined with the visual data. There are other types of data combinations, include image data of a familiar person obtained at block 805 combined with the $3^{rd}$ party data (e.g. a song, photos, videos, etc.). It will be appreciated that data can be combined according to currently known and future known approaches at block 812. In this way, response data from a $3^{rd}$ party source can be made to feel more personalized from the response data that is considered more personal.

Figure 8C:
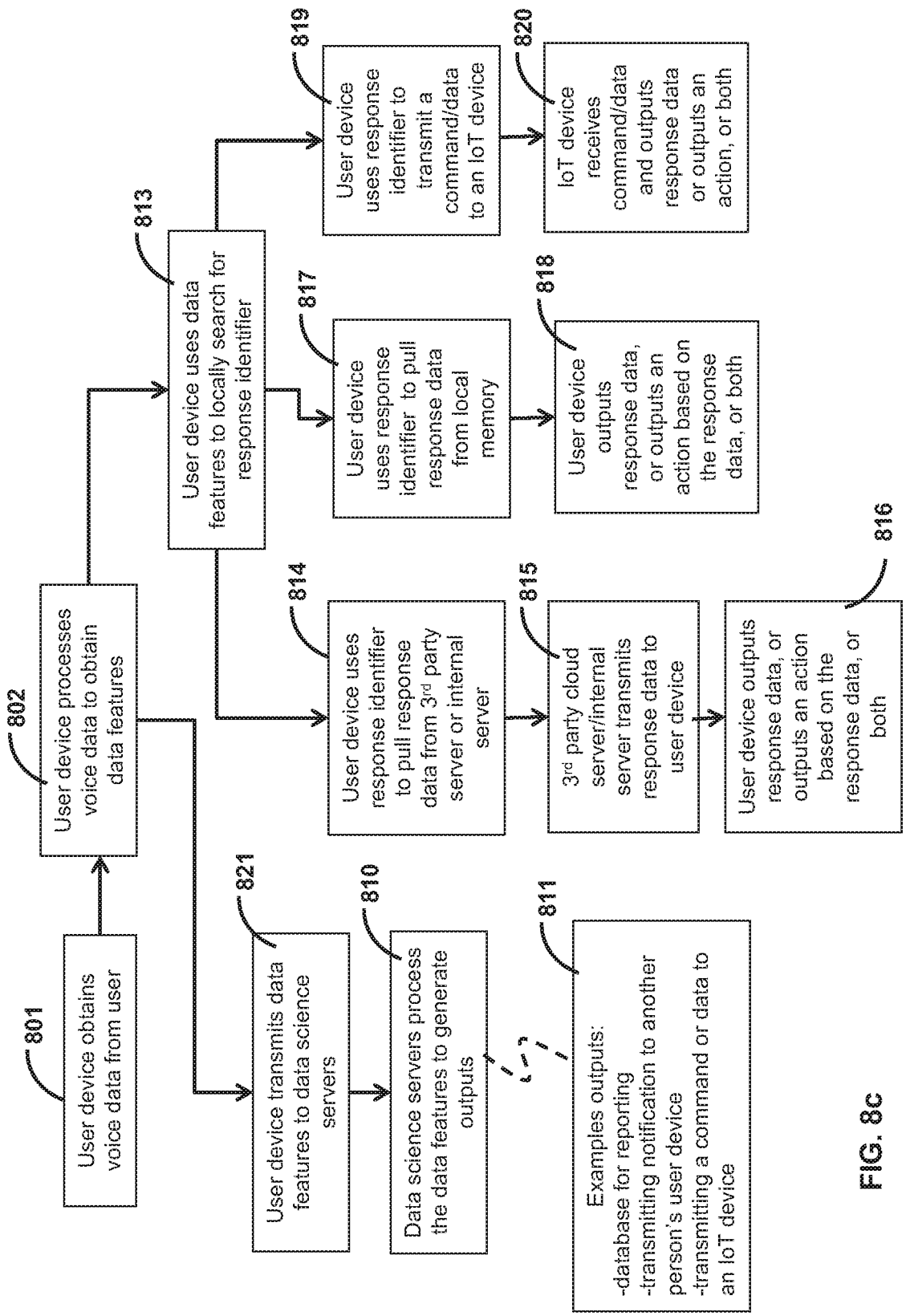

FIG. 8c shows another example embodiment that is similar to FIGS. 8a and 8b, but more of the computations are done locally on the user device. After block 802, the user device uses data features to locally search for a response identifier (block 813). Following block 813, one or more of the following sets of operations can take place: blocks 814, 815, 816; blocks 817, 818; and blocks 819, 820. Details of the blocks are below.

Block 814: User device uses response identifier to pull response data from 3rd party server or internal server. Block 815: 3rd party cloud server/internal server transmits response data to user device. Block 816: User device outputs response data, or outputs an action based on the response data, or both.

Block 817: User device uses response identifier to pull response data from local memory. Block 818: User device outputs response data, or outputs an action based on the response data, or both.

Block 819: User device uses response identifier to transmit a command/data to an IoT device. Block 820: IoT device receives command/data and outputs response data or outputs an action, or both.

In another example aspect, after block 802, the user device transmits the data features to the data science server (block 821). Following block 821, blocks 810, 811 are executed.

Figure 9:
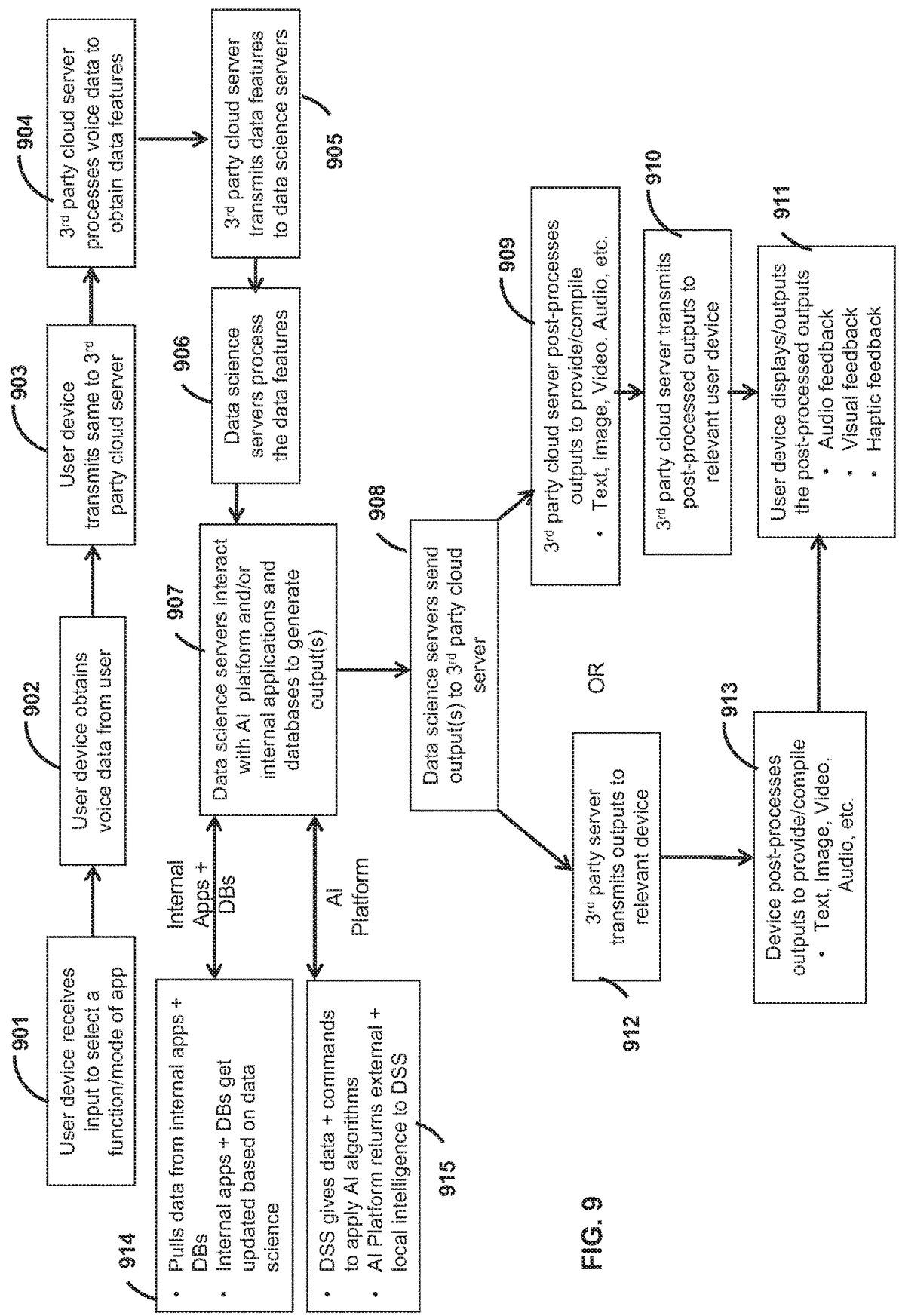
FIG. 9 is a flow diagram of executable instructions for processing voice data using a user device and further processing the data using the data enablement platform.

Turning to FIG. 9, example computer executable instructions are provided for processing data using the data enablement platform. In an example aspect, at block 901, a user device or an OCD, or both, receives input to select a function or a mode of an application (e.g. the data enablement application) that resides on the user device. Block 901 is optional. In an alternative embodiment, the user device is already in a listening state, ready to obtain voice data from a user without any immediately prior user input. At block 902, the user device or the OCD, or both, obtains voice data from a user. At block 903, the user device or the OCD, or both, transmits the same data to the $3^{rd}$ party cloud computing servers. The user device also transmits, for example, contextual data. At block 904, the $3^{rd}$ party cloud computing servers processes the voice data to obtain data features.

Non-limiting examples of extracted data features include text, sentiment, action tags (e.g. commands, requests, questions, urgency, etc.), voice features, etc. Non-limiting examples of contextual features include the user information, device information, location, function or mode of the data enablement application, and a date and time tag.

The extracted data features and the contextual features are transmitted to the data science servers (block 905). The original data (e.g. raw audio data, raw image data, etc.), or data representing the original data (e.g. vector representations, hash representations, compressed representations, etc.), may also be transmitted to the data science servers. At block 906, the data science servers process this received data.

At block 907, the data science servers interact with the AI platform, or the internal applications and internal databases, or both, to generate one or more outputs.

The data science servers then send the one or more outputs to the $3^{rd}$ party cloud computing servers (block 908). In one example embodiment, the $3^{rd}$ party cloud computing servers post-processes the outputs to provide or compile text, image, video or audio data, or combinations thereof (block 909). At block 910, the $3^{rd}$ party cloud computing servers transmit the post-processed outputs to the relevant user device(s) or OCD(s). At block 911, the user device(s) or the OCD(s), or both, output the post-processed outputs, for example, via an audio device or a display device, or both.

In an alternative embodiment, stemming from block 908, the $3^{rd}$ party cloud computing server transmits the outputs to the one or more relevant devices (e.g. user devices or OCDs) at block 912. The post-processing is then executed locally on the one or more relevant devices (block 913). These post-processed outputs are then outputted via audio devices or visual devices, or both on the one or more user devices or OCDs (block 911).

Turning back to block 907, in an example aspect, the data science servers pull data from the internal applications and internal databases, or the internal applications and internal database are updated based on the results produced by the data science servers, or both (block 914). These computations by the data science servers can also include accessing data from the Internet, social sites, and $3^{rd}$ party databases.

In another example aspect, the data science servers transmit data and commands to the AI platform, to apply AI processes on the transmitted data. In return, the AI platform transmits external and local information and data intelligence to the data science servers. These operations are shown in block 915.

It can be appreciated that any two or more of the operations in blocks 907, 914, and 915 can affect each other. In an example embodiment, the outputs of block 914 are used in the operations of block 915. In another example embodiment, the outputs of block 915 are used in the operations of block 914.

The data science servers 104 include a data science algorithms library and a policy and rules engine. For example, the policy and rules engine includes policies and rules that are specific to a person, a group, or an organization using the data enablement platform.

Regarding the data science algorithms library, it will be appreciated that data science herein refers to math and science applied to data in the form including but not limited to algorithms, machine learning, artificial science, neutral networks, etc. The results from data science include, but are not limited to, health and technical trends, recommendations, actions, trends, etc. While the algorithms and computations may reside in a library on the data science servers, copies of these libraries, or copies of portions of these libraries, are also stored on any one or more of: the user devices 102 and 111; the OCDs 301, 301a, 301b; the $3^{rd}$ party cloud servers 103; the AI platform 107; and IoT devices 115. In this way, these devices can locally perform machine learning (ML) and data science computations on the edge of the computing system. This allows for more responsive computing to a person with dementia who is interacting with a user device or OCD.

In an example aspect, Surface, Trend, Recommend, Infer, Predict and Action (STRIPA) algorithms are included in the data science algorithms library. This family of STRIPA algorithms worth together and are used to classify specific types of data science to related classes. Categories corresponding to the STRIPA methodology can be used to classify specific types of data or decision science to related classes, including for example Surface algos, Trend algos, Recommend algos, Infer algos, Predict algos, and Action algos. Surface algos, as used herein, may generally refer to data science that autonomously highlights anomalies and/or early new trends. Trend algos, as used herein, may generally refer to data science that autonomously performs aggregation analysis or related analysis. Recommend algos, as used herein, may generally refer to data science that autonomously combines data, metadata, and results from other data science in order to make a specific autonomous recommendation and/or take autonomous actions for a system, user, and/or application. Infer algos, as used herein, may generally refer to data science that autonomously combines data, metadata, and results from other data science in order to characterize a person, place, object, event, time, etc. Predict algos, as used herein, may generally refer to data science that autonomously combines data, metadata, and results from other data science in order to forecast and predict a person, place, object, event, time, and/or possible outcome, etc. Action algos, as used herein, may generally refer to data science that autonomously combines data, meta data, and results from other data science in order to initiate and execute an autonomous decision and/or action.

Non-limiting examples of other data science algorithms that are in the data science library include: Word2vec Representation Learning; Sentiment (e.g. multi-modal, aspect, contextual, etc.); Negation cue, scope detection; Topic classification; TF-IDF Feature Vector; Entity Extraction; Document summary; Pagerank; Modularity; Induced subgraph; Bi-graph propagation; Label propagation for inference; Breadth First Search; Eigen-centrality, in/out-degree; Monte Carlo Markov Chain (MCMC) simulation on GPU; Deep Learning with region based convolutional neural networks (R-CNN); Torch, Caffe, Torch on GPU; Logo detection; ImageNet, GoogleNet object detection; SIFT, SegNet Regions of interest; Sequence Learning for combined NLP & Image; K-means, Hierarchical Clustering; Decision Trees; Linear, Logistic regression; Affinity Association rules; Naive Bayes; Support Vector Machine (SVM); Trend time series; Burst anomaly detection; KNN classifier; Language Detection; Surface contextual Sentiment, Trend, Recommendation; Emerging Trends; Whats Unique Finder; Real-time event Trends; Trend Insights; Related Query Suggestions; Entity Relationship Graph of Users, products, brands, companies; Entity Inference: Geo, Age, Gender, Demog, etc.; Topic classification; Aspect based NLP (Word2Vec, NLP query, etc.); Analytics and reporting; Video & audio recognition; Intent prediction; Optimal path to result; Attribution based optimization; Search and finding; and Network based optimization.

In other example embodiments, the aforementioned data science can reside on the user's smartphone, or in public or private clouds, or at the employee's data center, or any combination of the aforementioned.

The above devices and systems are used to assist persons with dementia.

The state of dementia can vary from infrequent moments to progressively worse states of dementia throughout the day. Smart device(s) machine learn the patients progressions on a real time basis and autonomously begin providing increasingly more or less help me's, tell me's, show me's and autonomous IoT actions so that the dementia patient has as much or as little non-human help as required in order to be self-sufficient for that given day and dementia state. Providing too much assistance precludes the person from stretch goaling their memory and physical activity. Cached data science (ML, STRIPA algos) embedded in these smart devices provides patients with autonomous answers, recommendations and actions based on the patient's dementia state that moment, that morning, that day, etc. and can dynamically change these answers, recommendations, and actions using machine learning.

NLP can be performed to determine a patient's calmness, sadness, agitation, fear, frustration, happiness, etc. Based on the patient's current dementia state, the smart device can take an autonomous action(s) such as asking the patient if they would like to talk about a happy family trip he/she took 10 years ago or autonomously suggesting to play a family slide show video. In a preferred example embodiment, the NLP is computed locally on the smart device (e.g. the user device or OCD) so that computations can be applied to a patient's real time voice stream and a response can be given in real time. In another example, the NLP occurs the data enablement platform 303. It will be appreciated that other algorithms and other types of data can be used herein to detect a patient's mood and cognitive state. For example, sentiment analytics are used.

In an example aspect, a DSP voice synthesizer module resides in on the data enablement platform 303 and on the smart device(s) (e.g. user device 102, OCD 301, etc.). Non patient users can read a paragraph in their native tongue so that the cloud system can detect tones, utterances, timbre, pauses, etc. in order to synthesize this person's real voice. The intent is that any response in the digital library can be reproduced in the voice of a spouse, family member, friend, care giver, doctor, or health care provider. This is important because this calms the patient down and away from a fearful or agitated dementia state.

The NLP and DSP modules can be used in conjunction so that the NLP module listen's to the patient asking a question to a specific person, and then system and device(s) can (1) detect who the person that the patient is talking about, and (2) the system and device(s) can respond in the voice of that intended person.

The content for these answers, recommendations are input by the users and machine learned by the system and device(s). This information is stored in both the data enablement platform, below, as well as cached on the local device(s), below. Machine learning and caching are used to answer questions that are frequently being asked by the patient and consequently provides a much faster, lower latency response time to the patient's question and the overall conversation. The intent and goal is to provide a seemless, natural conversation between the patient and the local device so that the patient does not become frustrated by the pauses introduced by the system and device(s) due to compute time, query time, bandwidth issues, and storage issues.

Figure 10:
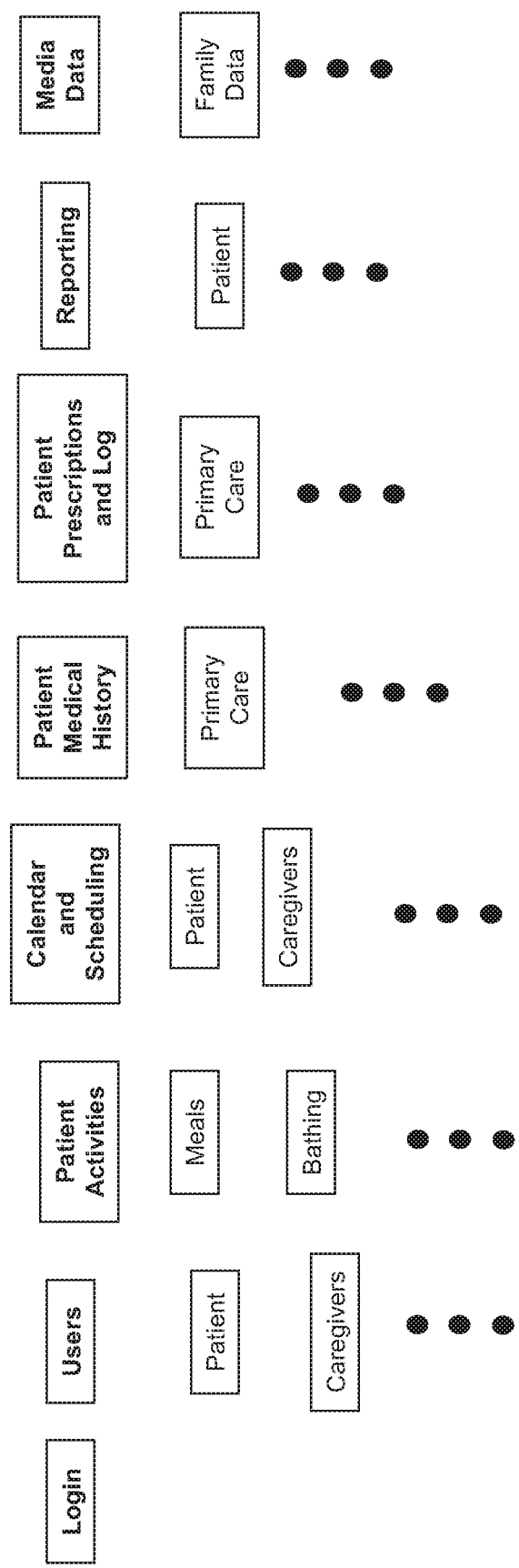
FIG. 10 is a block diagram of an example setup configuration of an information architecture.

Turning to FIG. 10, an example of a setup process and a configuration information architecture is shown. Various example libraries are shown, which can be stored on the data enablement platform 303.

Step 1: Create new account builds unique data stores, template libraries, accounts and AI bots. Examples of data stores include: Users store; Patient Activities store; Calendar and Scheduling store; Patient Medical History store; Patient Prescription store; and Multimedia store.

Step 2: Create new account builds a secured and personalized app to download to smart device(s).

Step 3: User enters patient(s), family members, friends, care givers, doctors, and other prof. health provider info that are related to patient(s)

Step 4: User assigns application feature and functionality accessibility

Step 5: System automatically sends message (email, text, phone call) to patient care givers requesting to enter login credentials and authenticate themselves Step 6: Each credentialed user prompted to enter picture of self, contact information, friends and related contact information (name, address, phone number) of patient(s), patient medical history, patient reports, patient interests areas (walking, drawing, going to the movies, food likes/dislikes, music, arts, photos etc.); links to social media sites (youtube/instagram/fb slides shows, videos), links to favorite music stations Step 7: Users enter doctor appointments, family get together dates, daily activities (walking, meals, movies, afternoon activities, field trips), etc.

Step 8. Users can view daily activity reports. Reports driven by multiple systems including, for example: Wearable sensors; Room IoT sensors; Implant IoT sensors; Facility/home IoT sensors (doors, locks, elevators, tv, etc.); Smart device(s) that patient converses; Exercise, walk, slip, fall reports; and Inactive reports.

With respect to the user store, it will be appreciated that this contains information about credentialed users who can access the device(s) and the system configuration. The credentialed users are able to enter in a list of current and upcoming activities (e.g. in the patient activities store). The data in the patients activity store is used to orally inform a patient about upcoming activities and past activities.

The data in the calendar and scheduling store includes links to electronic calendars. Credentialed users are able to enter in event dates and time. The information in this data store is used to provide reminders to patients and caregivers in the form oral/audio output, email, text, images, or a combination thereof. The calendar events can also include data identifiers (e.g. data pointers, URLs, etc.) to output data at a pre-scheduled date and time, or at a recurring pre-scheduled dates and times (e.g. daily, weekly, monthly, yearly, etc.). For example, a video is automatically played at the user device to the patient on a weekly basis.

With respect to the patient medical history store, credentialed users can enter, upload and review medical history.

With respect to the patient prescriptions and log, credentialed users can enter and review prescriptions. This information is used to remind caregivers and patients to take their medicine.

With respect to the reporting store, credentialed users can review STRIPA reports and non-STRIPA reports. These reports include behavior changes and anomalies that are surfaces or determined by AI computing algorithms. These reports also present recommendations to the caregivers or the patient, or both. These recommendations are determined by AI computations.

With respect to the picture/video/audio slideshow store, this aspect of the data stores includes links to social media sites. These links are activated or pulled using voice enabled commands from a user device (e.g. an OCD).

Figure 11:
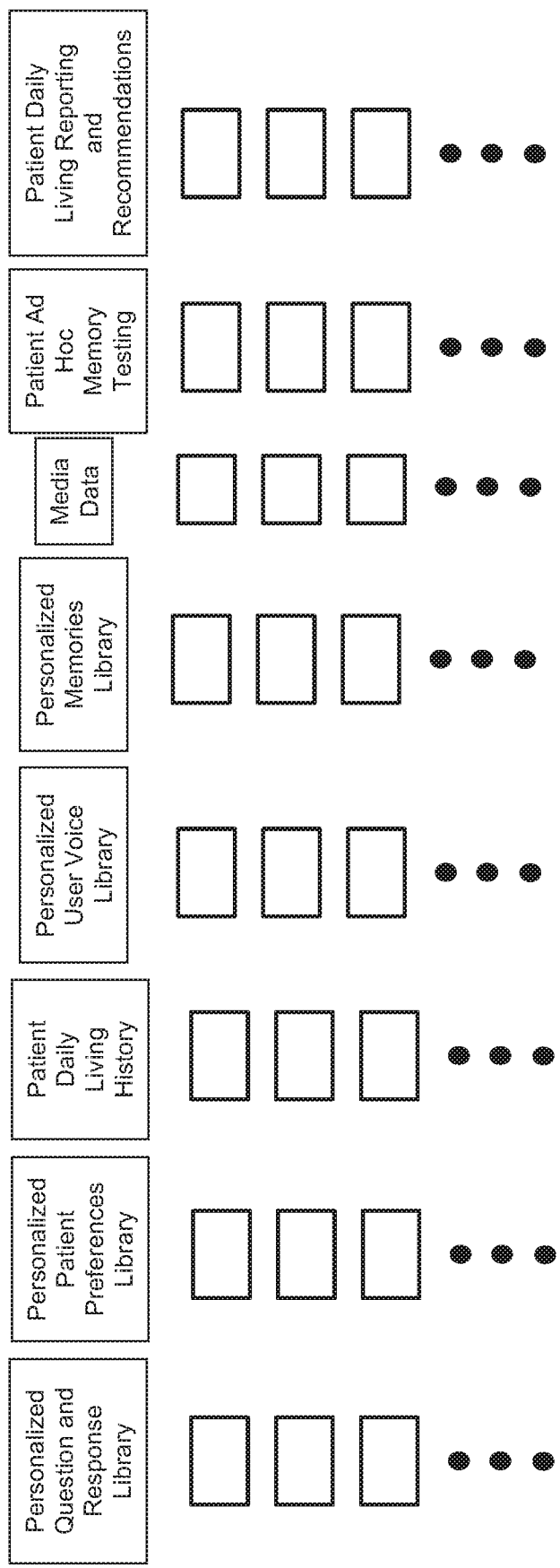
FIG. 11 is a block diagram of an example personalization configuration of an information architecture.

Turning to FIG. 11, an example of a personalization configuration architecture is shown.

In relation to the example embodiment in FIG. 11, the following are example steps for configuring a voice personalized library.

Step 1: User logs in

Step 2: User selects voice personalization. This includes, for example, the system initiating NLP to record and analyze user's voice tone, timbre, frequency and other audio voice attributes.

Step 3: User promoted to read a script from the screen while the NLP bot records the user's voice.

Step 4: Voice NLP bot decomposes tones, utterances, timbre, sound bytes into a template library.

Step 5: Voice synthesizer bot calls this specific user voice template library when patient converses with a specific person.

Step 6: Repeat these steps 1-5 for all family members, friends, doctors and health care providers.

In relation to the example embodiment in FIG. 11, the following are example steps for configuring personalized preference libraries.

Step 1: User logs in.

Step 2: User selects patient personalization.

Step 3: Application begins walking the user through various personalization templates requesting information. For example, the user can speak or type in information.

The following is a specific example.

a. A user selects personalized patient FAQ (frequently asked questions) bot.

b. The bot proceeds to ask the user: what is a question that your loved one asks?

c. User speaks or types in the question.

d. Bot proceeds to ask user: what is the answer to this question?

e. User speaks or types in the answer f. This process is repeated until completed g. These questions and answers can be revised or deleted in the future.

h. These questions can be autonomously added if NLP machine learning detects a new question that has not been previously asked by the patient. For example, these questions are then workflow sent to the appropriate family member, friend, doctor, care giver for a response. The bot will consequently provide a response to the patient.

These above steps a to h occur for each of the personalized preference libraries.

Personalized Preference Libraries include those displayed in diagram as well as the following examples.

The following are examples of "Tell Me FAQs" stored in a library.

A device detects a person saying: Tell me who that person is. In response, a wearable device worn by patient takes picture of person and then wirelessly transmits who that person to the patients hearing aid or ear buds.

A device detects a person saying: Tell me where I am at. In response, a wearable device worn by patient that has GPS mapping functionality and then wirelessly transmits where the person is to the patient's hearing aid or ear buds.

A device detects a person saying: Tell me when to go to the doctor's appointment. In response, a conversation is initiated using a synthesized caregiver's familiar voice via a smart device.=, with the person.

A device detects a person saying: Tell me when I see my son/daughter next. In response, a conversation is initiated using a synthesized caregiver's familiar voice via a smart device, with the person.

A device detects a person saying: Tell me when dinner is served. In response, a conversation is initiated using a synthesized caregiver's familiar voice via a smart device, with the person.

A device detects a person saying: Tell me what my daughter's birth date is. In response, a conversation is initiated using a synthesized daughter's voice via a smart device, with the person.

A device detects a person saying: Tell me what I am supposed to be doing right now. In response, a conversation is initiated using a synthesized caregiver's familiar voice via a smart device, with the person.

A device detects a person saying: Tell me what I am supposed to do today, this afternoon, tomorrow. In response, a conversation is initiated using a synthesized caregiver's familiar voice via smart device, with the person.

A device detects a person saying: Tell me to take shower, brush teeth, comb hair. In response, a conversation is initiated using a synthesized caregiver's familiar voice via smart device, with the person.

A device detects a person saying: Tell me how to get to the bathroom. In response, a conversation is initiated using a synthesized caregiver's familiar voice via a smart device, with the person.

A device detects a person saying: Do I have enough money to buy groceries? In response, a conversation is initiated using a synthesized son's voice (e.g. son of the person) via a smart device, with the person.

A device detects a person saying: Do I have enough money to pay rent? In response, a conversation is initiated using a synthesized son's voice (e.g. son of the person) via a smart device, with the person.

A device detects a person saying: Did I file my tax return? In response, a conversation is initiated using a synthesized daughter's voice (e.g. daughter of the person) via a smart device, with the person.

A device detects a person saying: Where is my dog? cat? In response, a conversation is initiated using a synthesized caregiver's familiar voice via a smart device, with the person.

A device detects a person saying: Who buys my groceries? In response, a conversation is initiated using a synthesized friend's voice (e.g. friend of the person) via a smart device, with the person.

A device detects a person saying: What time should I go to bed? In response, a conversation is initiated using a synthesized caregiver's familiar voice via a smart device, with the person.

A device detects a person saying: Where is my car? In response, a conversation is initiated using a synthesized son's voice via a smart device, with the person.

A device detects a person saying: How long will I have to stay here? In response, a conversation is initiated using a synthesized daughter's voice via a smart device, with the person.

The following are examples of actions in a Helping Library.

Autonomously alert caregiver where I am because I am outside my normal geography. A wearable device worn by patient that has GPS mapping functionality and then wirelessly transmits where the person is to the patient's hearing aid or ear buds.

Autonomously recognize who I am and unlock and open the door. A wearable device worn by patient that wirelessly unlocks the door and opens the door.

Autonomously flush the toilet. A wearable device worn by patient that wirelessly flushes toilet when patient orally asks to flush toilet.

Autonomously turn on the shower when I step in shower. A wearable device worn by patient that wirelessly turns shower on when patient orally asks to turn on shower.

Autonomously recognize who I am and request the elevator. A wearable device worn by patient that wirelessly prompts elevator when patient orally asks for elevator.

Remind me, privately, that my husband passed away, if I begin talking about him as he is alive.

How do I get home? A wearable device worn by patient that has GPS mapping functionality and then wirelessly transmits where the person is to the patient's hearing aid or ear buds.

The following are examples of actions stored in a Depressed/Sad NLP library,

If patient/loved one is depressed or sad, then smart device recognizes this through NLP and then initiate one or more of the following:

autonomously plays favorite uplifting music, videos, slides shows;

autonomously prompts patient about a favorite fond memory;

autonomously prompts patient if they would like to continue hearing their favorite audio book; and autonomously ask how their recent activities were (e.g. adult coloring, walk, craft, movie watched) went.

With respect to the Personalized Patient FAQ Library in FIG. 11, in an example aspect, there are a library of questions and answers frequently asked by a patient. The answers are provided by family members, doctors, friends, and caregivers. This creates a more familiar, relaxing and calm experience for the patient. This library incorporates NLP and voice synthesizer processing to recall the right person to answer the patient's question. When a patient asks a new question, a synthesized son's voice responds that he needs to find out the answer and get back to the patient.

With respect to the Personalized Patient Preferences Library, the Patient Daily Living History library, the Patient Fond Memories Library, the Picture/Video/Audio/Multimedia Slideshow library, and the Patient Ad Hoc Memory Testing library, as shown in FIG. 11, in an example aspect, these libraries capture, store and present personalized content. This personalized content adds contextual oral content as a patient and a smart device converse with each other. These collected data are used for memory recall testing and brain exercises. The devices or the data enablement platform, or both, use NLP to detect calm, happy, aggressive, depressed and other states of a patient to make recommendations to care givers. The devices or the data enablement platform, or both, also applies NLP results to drive uplifting conversations and notify loved ones, care givers, doctors, etc. The devices or the data enablement platform, or both, apply summarizing computations to recorded conversations between a patient and a smart device, these summarized conversations are used as inputs by the smart device for future conversations with the patient. The devices or the data enablement platform, or both, apply machine learning to determine the conversations that are uplifting and not depressive or negative.

With respect to the Personalized User Voice Libraries in FIG. 11, in an example aspect, this library of user voices is used so that the patient can converse with, what appears to the patient to be, a specific person instead of a generic computer voice (e.g. a Siri voice). This creates a more familiar, relaxing and calm experience for a patient. Users (e.g. a son, a spouse, a caregiver, a doctor, etc.) read a script so that NLP and voice synthesizer modules learn each of the user's audio voice attributes. As a result, when a patient asks a question to a son, for example, the smart device responds using a synthesized voice that sound like the patient's son.

Continuing with FIG. 11, there are is a Patient Daily Living Reporting and Recommendations library. It includes Application Family/Relatives/Friends Use Cases. These use cases include, for example: autonomously tracking and reporting daily living slips and fall statistics; autonomously daily tracking and reporting daily living eating changes; autonomously GPS tracking and machine learning daily living where the loved one is and warn if outside a geo or behavioral (inactive) zone; autonomously reminding, tracking, and reporting prescription medicines; autonomously reminding to give certain foods at certain meals to loved one; autonomously tracking and reporting daily living number of steps taken each day; autonomously tracking and reporting daily living exercise done each day; autonomously tracking and reporting how much brain building time spent each day (adult coloring, cross word puzzle, sudoku, etc.); autonomously tracking and reporting blood pressure, pulse, seizures, glucose, other vital signs; autonomously sending reports and updates to primary physician and neurologist; autonomously sending emergency notifications (calls, emails, texts) to doctors, family, relatives, when an aforementioned use case is outside the normal expected behavior or physiological pattern, or both; and autonomously recommending new actions and suggestions to family, relatives, and friends based on new and trending memory loss behaviors and or psychological emerging patterns.

The Patient Daily Living Reporting and Recommendations library also includes dementia uses cases. Examples of these use case include: tracking; autonomously tracking slips and falls statistics of the patient; autonomously tracking the location of the patient (e.g. using GPS or other positioning systems, or a combination thereof); autonomously reminding the patient to take my prescription medicines; autonomously tracking foods the patient ate at each meal; autonomously tracking the number how many steps the patient walked each day; autonomously tracking how much exercise the patient did each day; autonomously tracking how much brain building exercises the patient spent each day (e.g. adult coloring, cross word puzzle, sudoku, etc.); and autonomously tracking the patient's blood pressure, pulse, seizures, glucose, and other vital signs.

Below is an example operation of a smart device. In an example embodiment, the smart devices or the data enablement platform, or both, dynamically update patient specific dementia data science, data and recommendations in order to provide smart devices with highly personalized track me, help me, tell me, and show me use case recommendations. These updated data science computations, data and recommendations that are specific to a given patient are locally loaded onto the smart device belonging to the patient.

Operation 1: The data enablement platform obtains Smart Device dementia daily living data science and converts it to FPGA/GPU based microcode.

Operation 2: Transmit dementia daily living data science, data, and recommendations real time over network(s) to a given Smart Device, or multiple ones. For example, these computations and data are transmitted of an Intelligent Transceiver, as described in PCT/US2018/022616 filed on Mar. 15, 2018.

Operation 3: Smart Device listens real time for new edge data science and downloads the new data science, data and recommendations Operation 4: Smart Device Transceiver(s) installs or "flashes" the new data science into FPGA/GPU, or the data, or the recommendations, or combinations thereof, to the local smart device data store, in real time. In an example, "hot" data is flashed to the faster access memory 1502 and the "medium" data is flashed to the slower access memory 1503. Data links or index addresses to data stored in the data enablement platform is stored to the memory module 1503a.

Operation 5: Smart Device operationalizes dementia data science, data libraries, and recommendations (help me, tell me, show me, remind me, perform automated actions and tasks etc.) using the latest data science, data and recommendations.

Operation 6: Smart Device performs local, autonomous actions based upon the data processed on the daily living actions by the dementia patient (help me, tell me, show me, remind me, perform automated actions and tasks etc.).

Operation 7: Smart Device applies data science including, voice NLP, algos, neural nets to detect new trends and actions, which are subsequently updated into the patient's corresponding cloud system account so that new data science, data, and recommendations are applied.

Operation 8: This autonomous action dynamically helps the dementia patient as the dementia changes from one state of dementia to another level of dementia Operation 9: Smart Devices utilizes voice synthesizers that mirror family members, care givers, friends, doctors, and health care professionals when the patient converses with the smart device.

Conversing in familiar voices calms the patient and makes the patient feel more secure.

Below are example aspects of the smart devices.

Patient smart devices are, for example, worn, implanted into body, surface attached to body, residing in living areas where dementia patients live, walk, and interact geographically. in or with the dementia software. Examples of these smart devices include instance of the following or combinations of the following: smart watches; smart phones; laptops; workstations; tablet devices; home assistant devices (e.g. like Google Home devices); smart devices embedded in, or part of, clothing, shoes, jewelry, glasses, or the like; smart devices attached to surface of skin (e.g. smart hearing aids, smart headphones/buds, smart EKG sensors, smart skin absorbing medical prescription release devices, smart heart/blood pressure monitoring devices, etc.); smart devices implanted into the human body (e.g. brain, organ, tissue); glucose monitor and release devices; seizure monitoring and prevention electrical charge intervention devices; irregular heart monitor and charge intervention devices; capture and remind stimulus devices; and smart machines integrated into daily objects (e.g. dispensing prescriptions, foods, fluids, door way gates, beds, toilets, sinks, showers, elevators, doors) and that intelligently recognize who the patient is, validate the patient, and perform an action or task.

These dementia related devices are collectively known as smart edge devices/nodes, which help patients autonomously capture and track information in their surroundings and autonomously and increasingly provide personalized and dynamically changing tell me's, help me's, show me's use cases and autonomous actions (unlock and open door) as the dementia patient memory dynamically changes throughout the day. These smart devices can have onboard computing, storage, data science, communication, sensors, user screens, audio (talk/listen), haptic sensors and haptic feedback devices, electrical stimulus in order to provide visual and oral reminders and or take autonomous actions (e.g. open door, flush toilet, etc.).

In an example embodiment, smart devices, systems and methods are provided that make distributed, decision science based recommendations and actions and that increasingly makes smarter recommendations and actions over time. Intelligent edge nodes include the devices that interact with persons with dementia. In an example embodiment, the intelligent edge nodes also include servers, server systems, subsystems, and or combinations of the aforementioned in conjunction with Intelligent Network(s) and Device(s). These intelligent edge nodes and intelligent networks have data science at the edge node computers and network links in order to identify, at the earliest points, eminent trends and recommend preemptive healthcare and technical actions sooner and faster than legacy and existing methods and systems.

Data science includes but is not limited to individual and combinations of algorithms (algos), machine learning (ML), and artificial intelligence (AI), to name a few. This data science can be embedded, for example, as microcode executing inside of processors (CPUs, GPUs, FPGAs, ASICs), scripts and executables running in operating systems, applications, subsystems, and any combinations of the aforementioned. Additionally, this data science can run as small "micro data science" software residing in static and dynamic RAM memory, EPROMs, solid state and spinning disk storage, and aforementioned systems that span N number of nodes with the aforementioned memory types and with N different types of memory types. These devices and systems can include block chain/immutable communication and ledgers in order to provide secured information about a dementia patient that is shared with family, relatives, caregivers, and physicians.

Each intelligent edge node has the ability to transmit and receive (e.g. transceive) new data science, software, data, and metadata to other edge nodes and 3rd party edge nodes so that real time or batch or manual data science and related data or meta data updates can potentially update the edge node(s) and 3rd party edge nodes in real time. Faster data science updates accelerate identifying eminent trends and recommend healthcare and technical actions.

Each intelligent edge node has the ability to automatically query other edge nodes and 3rd party edge nodes to determine if data science, data science results, etc. may exist on other intelligent edge nodes in order to accelerate making eminent trends and recommend preemptive daily living, medical and care giving actions.

Each intelligent edge node has data science to predict which other intelligent edge node(s) and intelligent network(s) and device(s) and or 3rd party edge node(s) most likely has the answer to questions summoned by the original edge node. This data science can then predictably force rank which nodes and networks to query. This predictably edge and network querying accelerates identifying eminent trends and making preemptive daily living, medical and care giving actions sooner and faster versus existing systems and methods.

Figure 12:
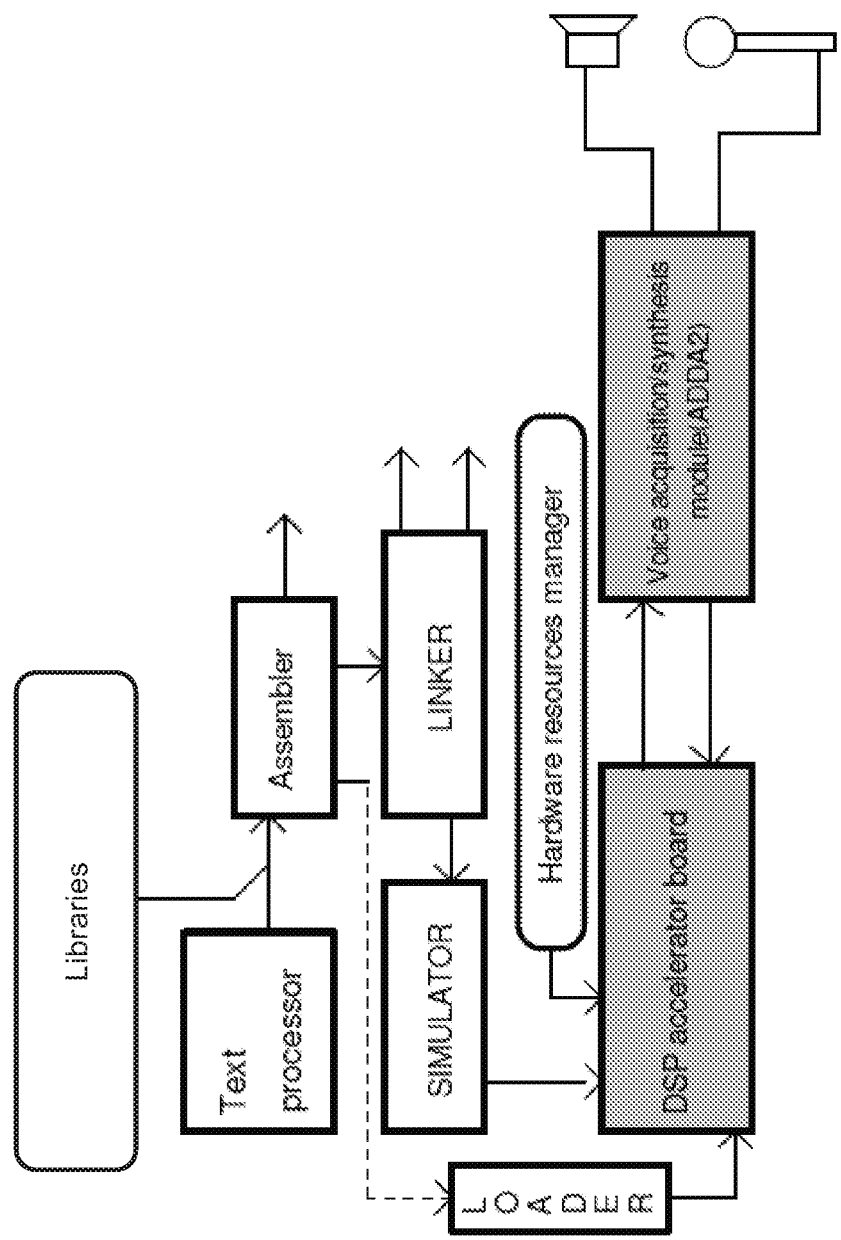
FIG. 12 is an example embodiment of a DSP-based voice synthesizer.

FIG. 12 shows an example of an onboard voice synthesizer. It is a DSP based system that resides on a smart device (e.g. the OCD or other device that converses with the patient). It includes one or more voice libraries as noted above. It also includes a text processor, an assembler, a linker module, a simulator, a loader, a DSP accelerator module which is managed by a hardware resources manager, and a voice acquisition and synthesis module (e.g. an analog/digital converter and digital/analog converter). The voice acquisition and synthesis module is in data communication with a microphone and an audio speaker.

Figure 13:
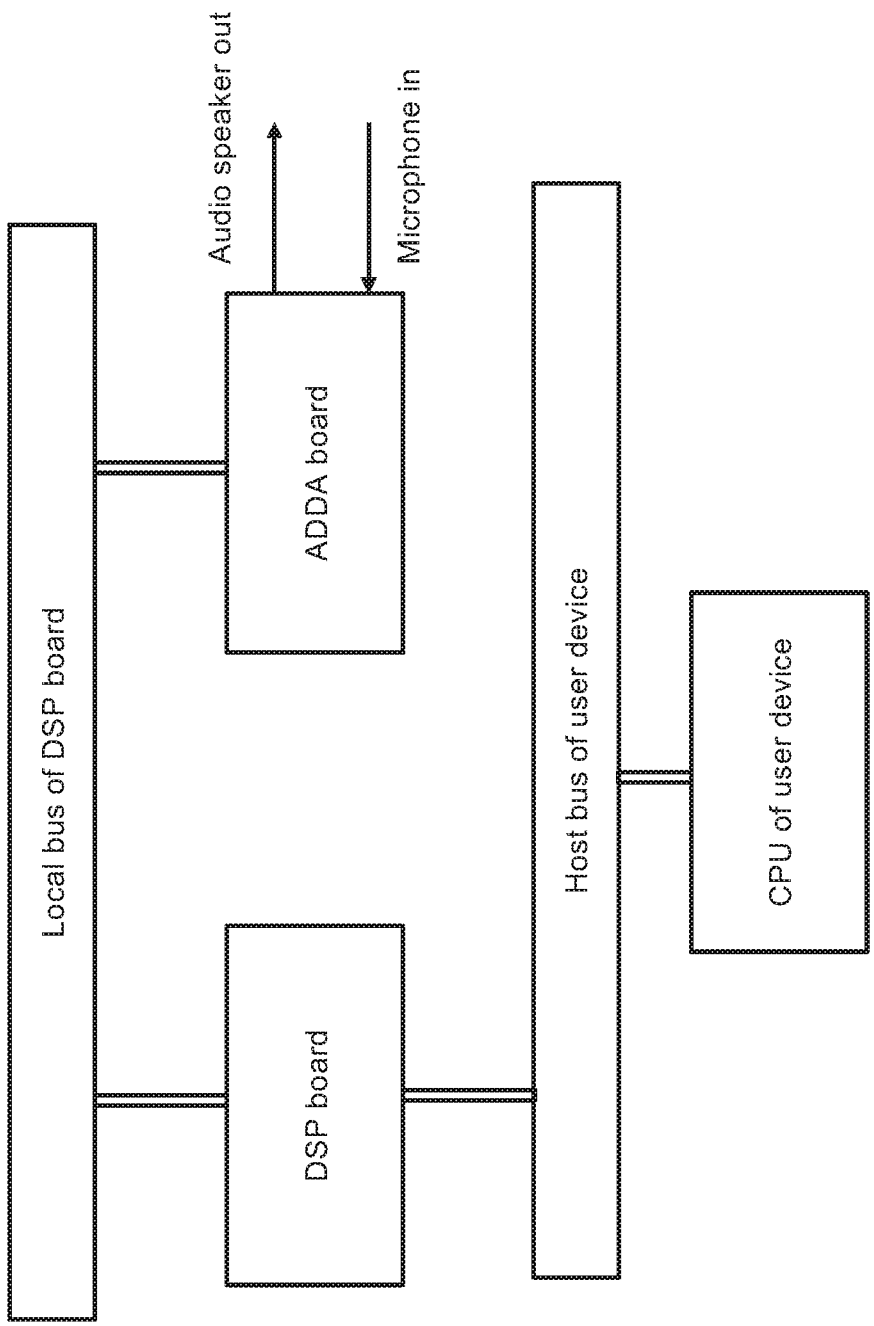
FIG. 13 is an example embodiment of a hardware system used by the DSP-based voice synthesizer.

FIG. 13 shows an example subset of components on a smart device, which includes a DSP board/chip, an ADDA2 board/chip, a local bus of the DSP board, a host bus, and a CPU of the smart device. These components, for example, support the software architecture shown in FIG. 12.

Figure 14:
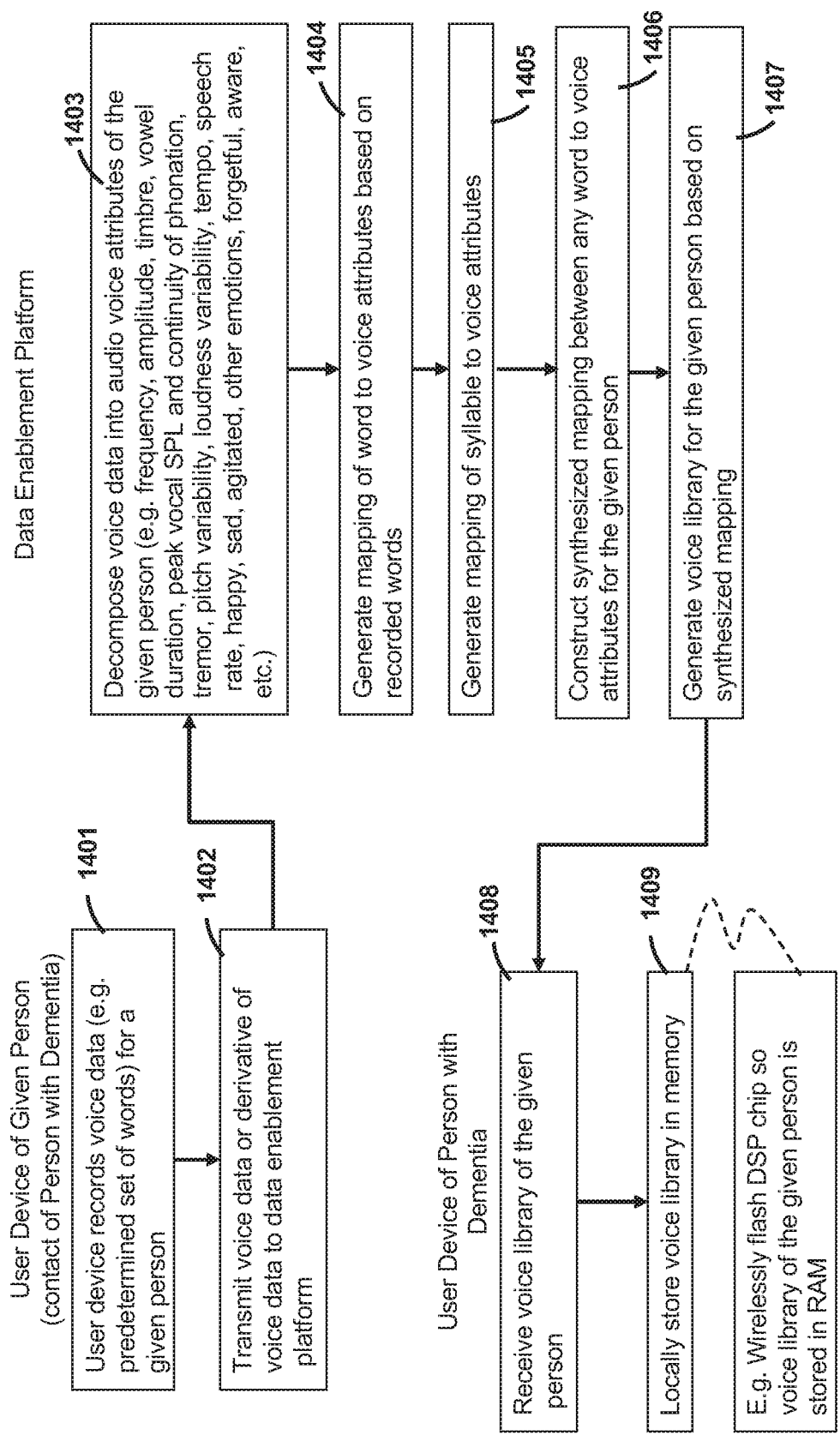
FIG. 14 is a flow diagram of example executable instructions for building a voice library of a contact of a person with dementia.

Turning to FIG. 14, example executable instructions are provided for building a voice library.

Block 1401: A user device of given person who is a contact of the patient (e.g. the caregiver, the daughter, the son, the spouse, etc.) records voice data of the given person. For example, the given person speaks a predetermined set of words.

Block 1402: The user device of the given person transmits the voice data or a derivative of voice data to the data enablement platform.

Block 1403: The data enablement platform decomposes the voice data into audio voice attributes of the given person (e.g. frequency, amplitude, timbre, vowel duration, peak vocal SPL and continuity of phonation, tremor, pitch variability, loudness variability, tempo, speech rate, etc.).

Block 1404: The data enablement platform generates a mapping of word to voice attributes based on recorded words.

Block 1405: The data enablement platform generates a mapping of syllable to voice attributes.

Block 1406: The data enablement platform constructs a synthesized mapping between any word to voice attributes for the given person.

Block 1407: The data enablement platform generates a voice library for the given person based on synthesized mapping.

Block 1408: The smart device that belongs to the patient receives the voice library of the given person.

Block 1409: The smart device of the patient locally stores the voice library in memory. For example, the system wirelessly flashes the DSP chip so that the voice library of the given person is stored in RAM on the smart device (block 1410). This data can also be stored in some other manner on the smart device.

Figure 15:
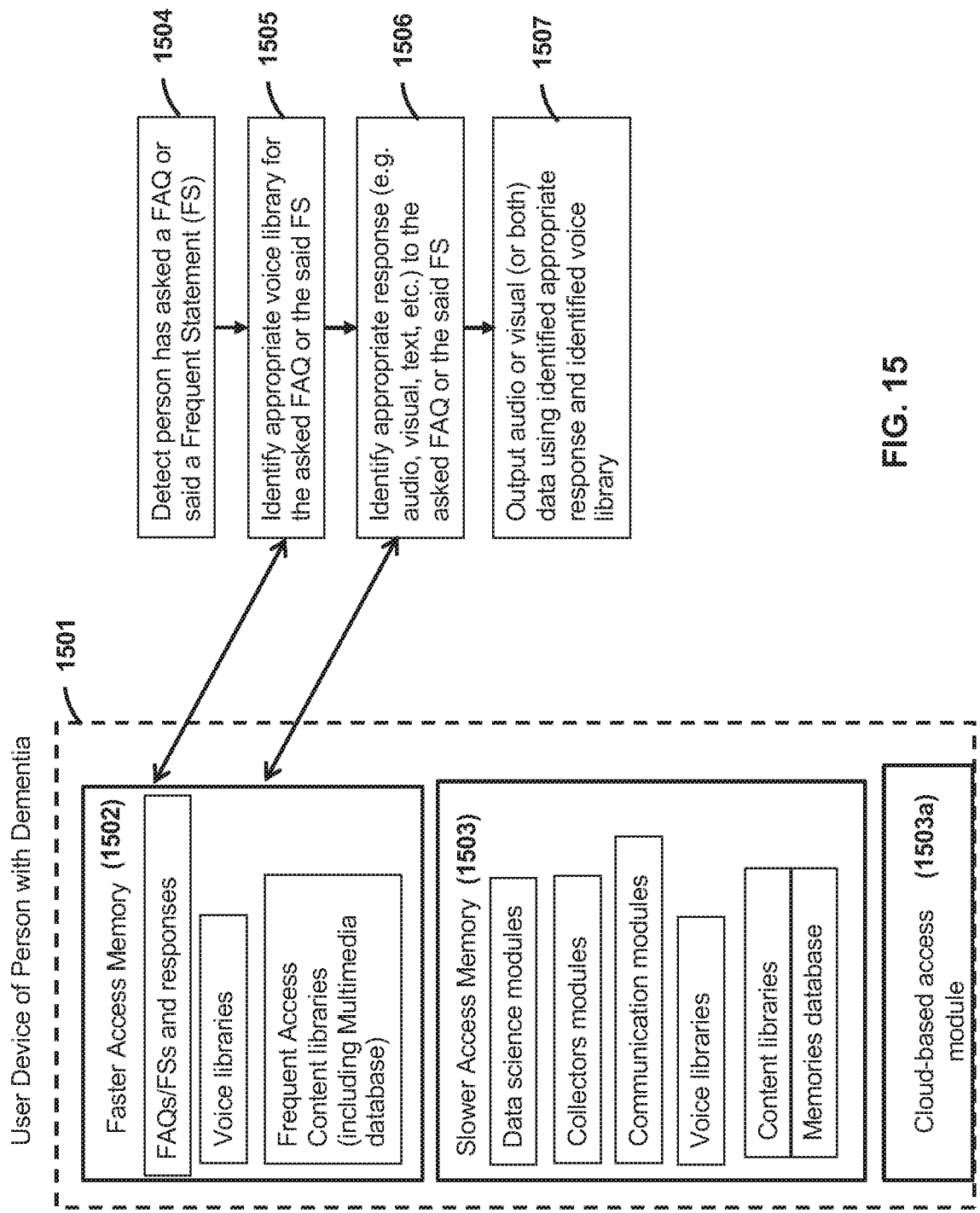
FIG. 15 is a flow diagram of example executable instructions for a smart device interacting with a person having dementia.

FIG. 15 shows an example of memory devices 1501 on a smart device of a patient. The memory devices include faster access memory 1502 and slower access memory 1503. In one example embodiment, the faster access memory is RAM and the slower access memory is ROM. Other combinations of faster and slower memory devices can be used in alternative to RAM and ROM.

The faster access memory 1502 has stored on it, amongst other things, a library of frequently asked questions (FAQs) and frequent statements (FSs), and corresponding responses to these FAQs and FSs. The faster access memory also has stored on it voice libraries of persons who interact with the patient, and a frequently accessed content libraries. These frequently accessed content libraries include multimedia. The information or content stored in memory 1502 provides local, edge, fast "hot" reacting content that is frequently needed, so that there is no need to go to the data enablement platform for same known-known data.

The slower access memory 1503 includes, amongst other things: data science modules, collectors modules, communication modules, other voice libraries, content libraries, and memories databases. The information or content stored in memory 1503 provides local, edge, fast "medium" reacting content that is needed, but not as frequently or immediately, so that there is no need to go to the data enablement platform for same known-known data.

Another data module, whether stored in 1503 or some other memory device allows for the smart device to interact with the data enablement platform to access content libraries. This is also called cloud "cold" reacting content that is relatively less frequently used.

Block 1504: The smart device detects a person has asked a FAQ or said a FS.

Block 1505: The smart device accesses the faster access memory 1502 and identifies an appropriate voice library for the asked FAQ or the said FS.

Block 1506: The smart device accesses the faster access memory 1502 and identifies the appropriate response (e.g. audio, visual, text, etc.) to the asked FAQ or the said FS.

Block 1507: The smart devices output audio or visual (or both) data using the identified appropriate response and the identified voice library. In this way, responses to FAQs and FSs occur very quickly, or even in real time, so provide a conversation like experience.

Figure 16:
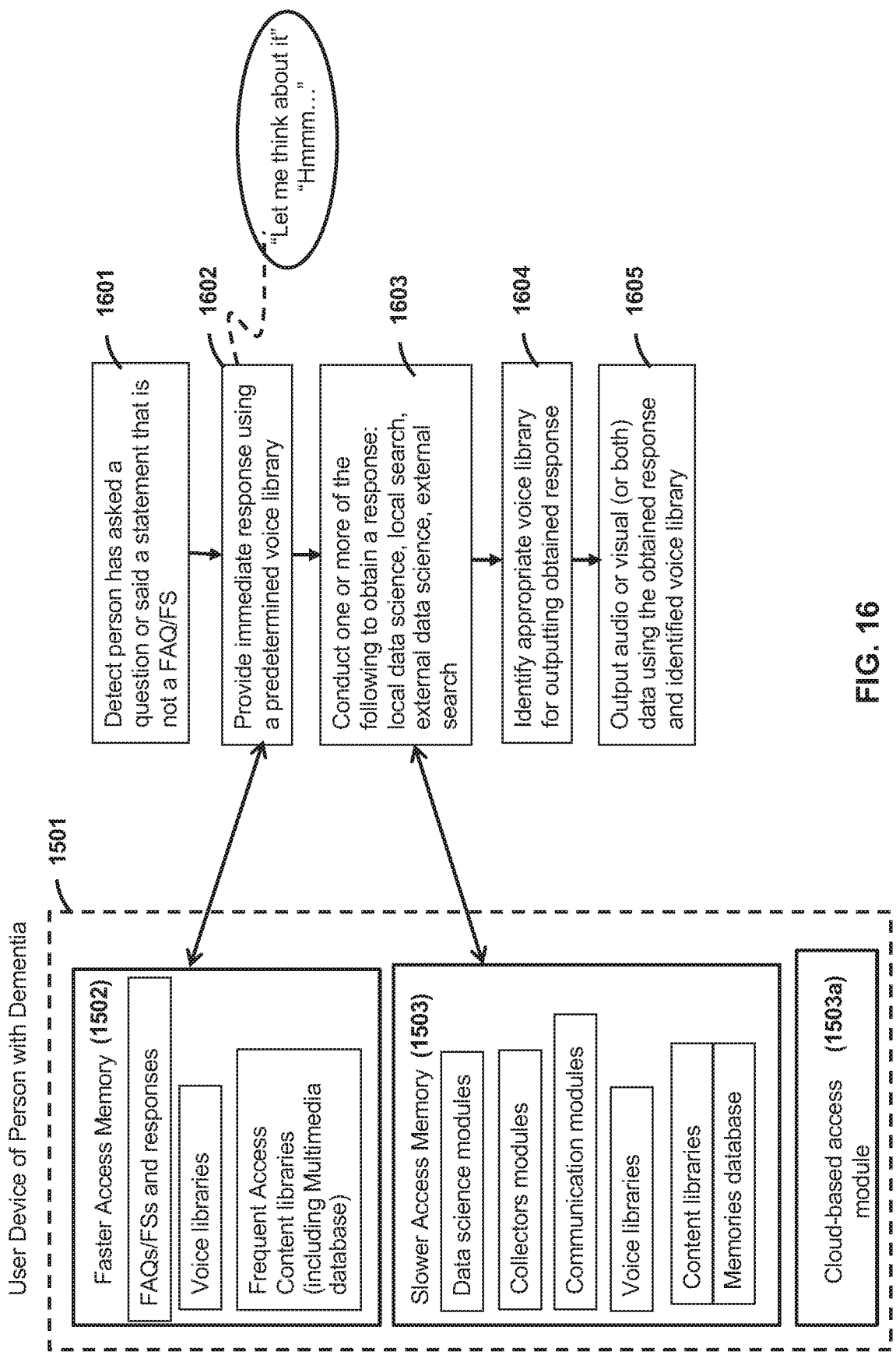
FIG. 16 is a flow diagram of example executable instructions for a smart device interacting with a person having dementia.

Turning to FIG. 16, another example set of executable instructions are executed by the smart device of the patient.

Block 1601: The smart device detects the person has asked a question or said a statement that is not a FAQ/FS.

Block 1602: The smart device provides an immediate response using a predetermined voice library. For example, the smart device says "Let me think about it" or "Hmmm". This response, for example, is preloaded into the faster access memory 1502 for immediate retrieval.

Block 1603: The smart device conducts one or more of the following to obtain a response: local data science, local search, external data science, and external search. This operation, for example, includes accessing the slower access memory 1503.

Block 1604: The smart device identifies an appropriate voice library for outputting the obtained response.

Block 1605: The smart device outputs audio or visual (or both) data using the obtained response and identified voice library.

In this way, more complex algorithms are computed locally on the smart device, either in part or in whole, while still providing an immediate response.

Figure 17:
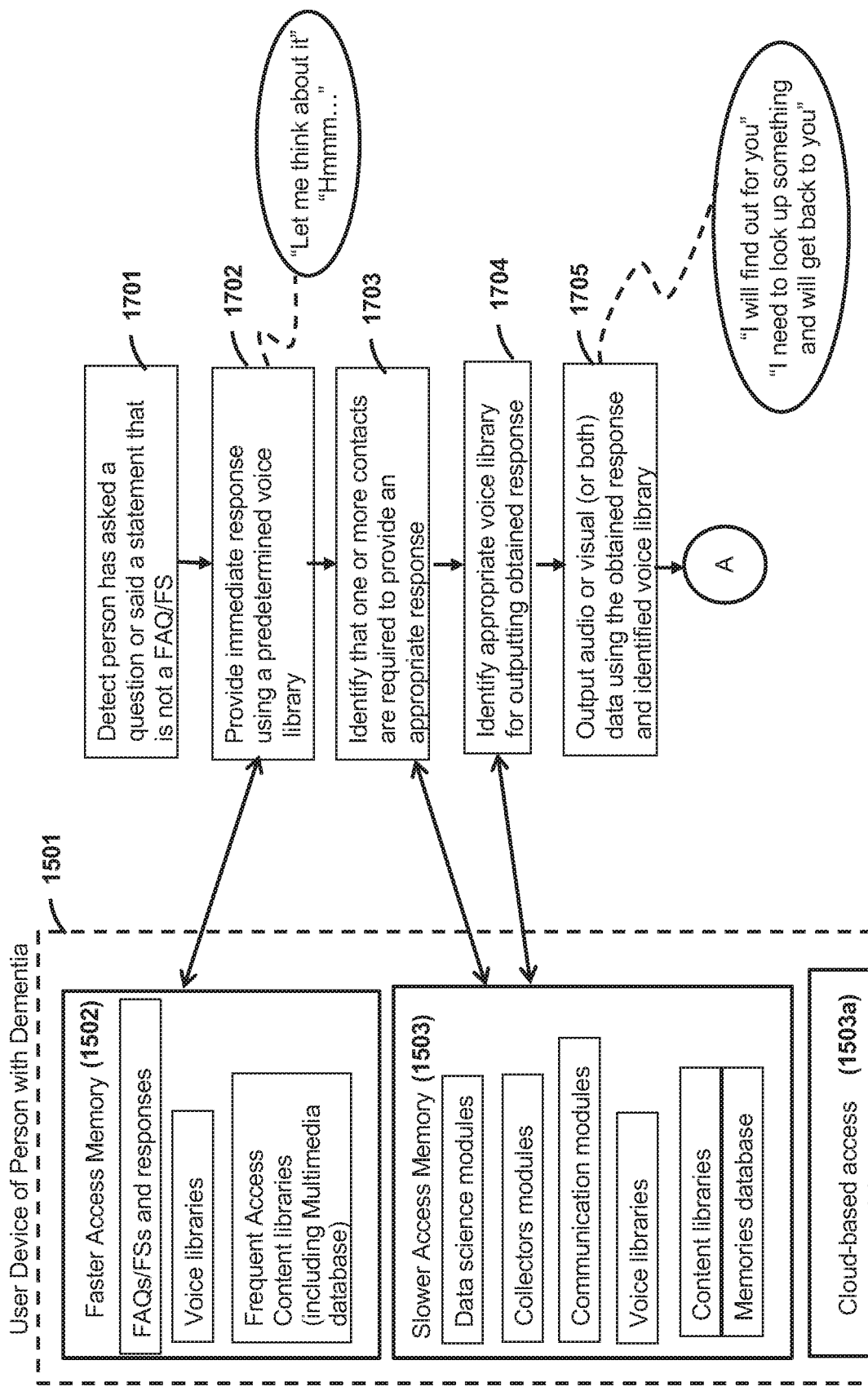
FIG. 17 is a flow diagram of example executable instructions for a smart device interacting with a person having dementia.
Figure 18:
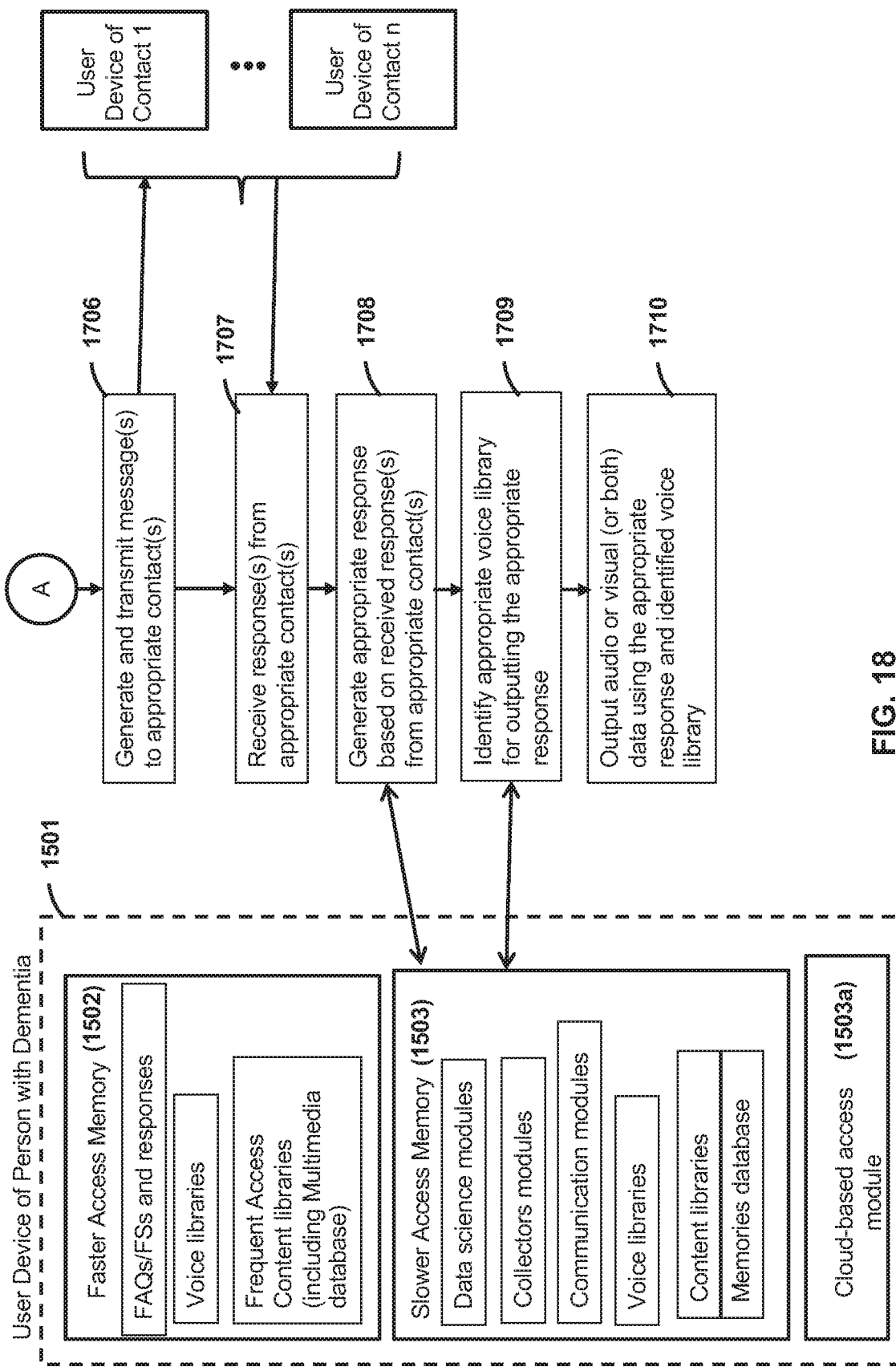
FIG. 18 is a flow diagram of example executable instructions for a smart device interacting with a person having dementia.

FIGS. 17 and 18 show another example embodiment of executable instructions executed by a smart device of a patient. If an answer to a patient's question or statement is not known, then the smart device initiates a message or communication session with a computing device belonging to a caregiver, son, daughter, spouse or other contact of the patient.

Block 1701: The smart device detects that the patient has asked a question or said a statement that is not a FAQ/FS.

Block 1702: The smart device provides an immediate response using a predetermined voice library. For example, the smart device accesses the faster access memory 1502.

Block 1703: The smart device identifies that one or more contacts are required to provide an appropriate response. For example, the smart device accesses the slower access memory 1503 to obtain this information.

Block 1704: The smart device identifies an appropriate voice library for outputting obtained response. For example, the smart device accesses the slower access memory 1503 to obtain this information.

Block 1705: The smart device outputs audio or visual (or both) data using the obtained response and identified voice library. For example, the smart device says: "I will find out for you" or "I need to look up something and will get back to you".

Block 1706: The smart devices generates and transmits message(s) to appropriate contact(s).

The one or more user devices of the contact then receive responses from the contacts (e.g. the caregiver, the son, the daughter, the spouse, etc.). For example, the contact receives a text message, phone call, video call, etc. in relation to the message from the smart device of the patient, and Block 1707: The smart device receives response(s) from appropriate contact(s).

Block 1708: The smart device generates appropriate response based on received response(s) from appropriate contact(s).

Block 1709: The smart device identifies the appropriate voice library for outputting the appropriate response.

Block 1710: The smart device outputs audio or visual (or both) data using the appropriate response and identified voice library.

In this way, the response from the one or more contacts are relayed back to the smart device of the patient.

In an example embodiment, new questions and statements and their respective responses are stored in memory for future retrieval. If the given new question or statement is detected more than a certain number of times within a certain time frame, then the given new question or statement and the corresponding response is stored in the faster access memory 1502 for fast retrieval.

Figure 19:
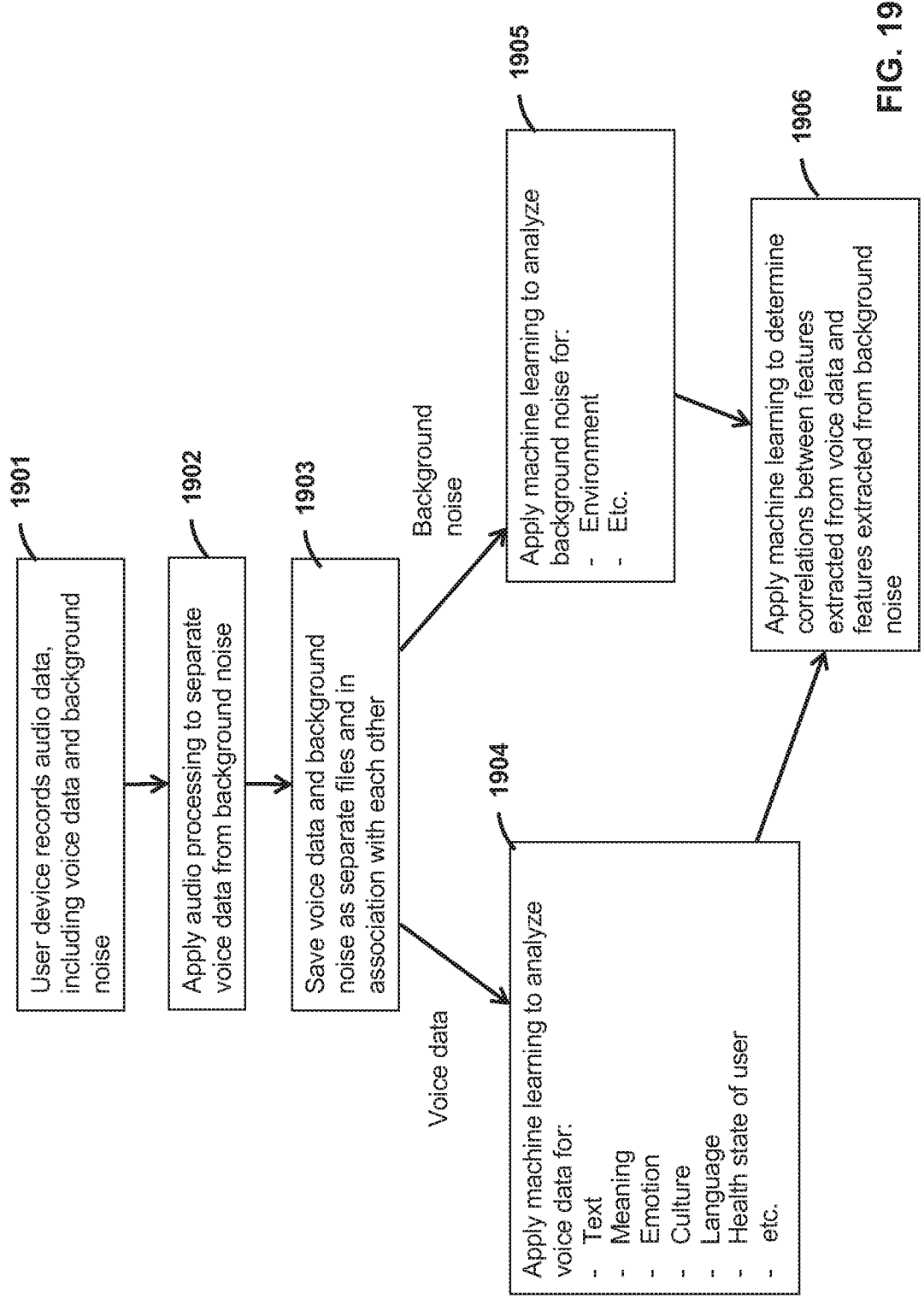
FIG. 19 is a flow diagram of example executable instructions for using the data enablement platform to extract data features from voice data and associated background noise.

Turning to FIG. 19, example executable instructions are provided for processing voice data and background noise.

Block 1901: The user device or the OCD records audio data, including voice data and background noise.

Block 1902: The data enablement platform applies audio processing to separate voice data from background noise.

Block 1903: The data enablement platform saves the voice data and the background noise as separate files and in association with each other.

Block 1904: The data enablement platform applies machine learning to analyze voice data for: text; meaning; emotion; culture; language; health state of user; etc.

Block 1905: The data enablement platform applies machine learning to analyze background noise for: environment, current activity engaged by user, etc.

Block 1906: The data enablement platform applies machine learning to determine correlations between features extracted from voice data and features extracted from background noise.

In this way, information about the user can be more accurately determined, such as their behavior and their surroundings. This in turn can be used provide sales opportunities that are better customized to the user.

Figure 20:
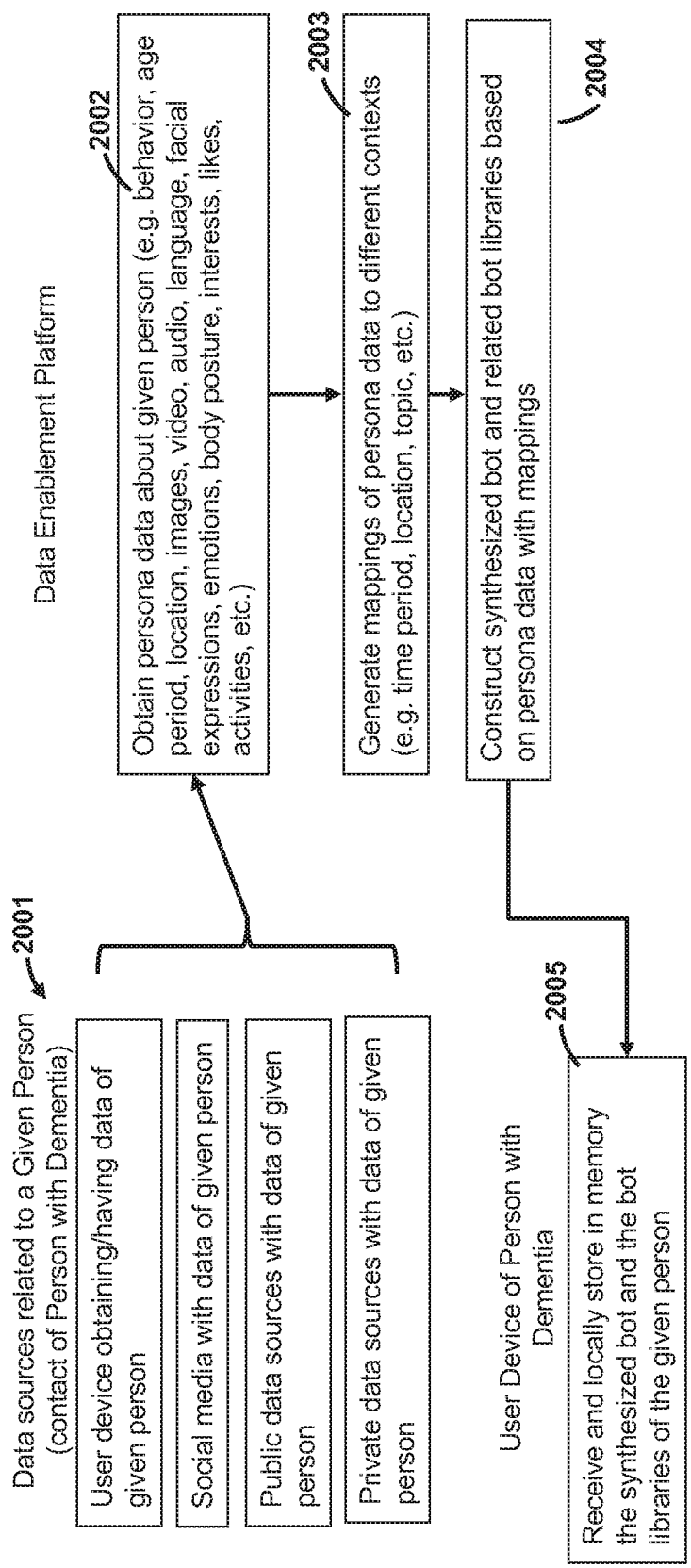
FIG. 20 is a flow diagram of example executable instructions for establishing a synthesized bot of a contact of a person who has dementia.

Turning to FIG. 20, an example embodiment is provided for a data enablement platform interacting with a user device of a person with dementia. At block 2002, the data enablement platform obtains persona data about given person (e.g. behavior, age period, location, images, video, audio, language, facial expressions, emotions, body posture, interests, likes, activities, etc.). The given person is a contact of the person with dementia (e.g. a family member, a friend, etc.). The persona data can come from different data sources 2001. Examples include the user device of the given person; social media with data of the given person; public data sources; and private data sources. At block 2003, the data enablement platform generates mappings of persona data to different contexts (e.g. time period, location, topic, etc.). For example, the given person is a daughter of a father who has dementia. The persona data of the daughter includes images, video, audio data, 3D images, text data, etc. This persona data is mapped to the context of different time frames when the daughter was a young girl, a teenager, a young woman, and present day as a middle-aged woman. Furthermore, mapped to each time frame are location data, topic data, etc.

At block 2004, a synthesized bot and related bot libraries are constructed based on the persona data with the mappings. The synthesized bot, for example, is a bot that uses one or more images, video, audio data, text data, etc. The synthesized bot, for example, uses synthesized voice data. In another example, the synthesized bot is synthesized avatar that looks, moves and speaks like the given person according to the different time frames (e.g. an avatar of the daughter when she is a young girl; a teenager; a young woman; and present day as a middle-aged woman). It will be appreciated that the bot libraries are used to vary the data and behavior of the synthesized bot. For example, when the synthesized bot uses a library of the daughter as a young girl, the bot would output one or more of images, audio, video, etc. of the daughter in that time frame from long ago. For example, when the synthesized bot uses a library of the daughter as a middle-aged woman, the bot would output one or more of images, audio, video, etc. of the daughter in the more recent time frame.

At block 2005, the user device of the person with dementia receives and locally stores in memory the synthesized bot and the bot libraries of the given person.

In this way, the synthesized bot of the given person (e.g. the daughter) can response in a manner that is contextually relevant to the perceived reality of the person with dementia (e.g. the father) who may live in the past.

In an example embodiment, the synthesized bot of the given person is shown as still image of the given person. In another example, the synthesized bot is shown as a moving image of the given person (e.g. also called a deepfake). For example, a deepfake is a technique for human image synthesis based on artificial intelligence. It is used to combine and superimpose existing images and videos onto source images or videos using a machine learning technique called a generative adversarial network (GAN).

In another example, the synthesized bot of the given person is a holographic image of the given person. 2D images from photos or videos, or both, are used to create 3D rendering. In another example, other imaging means (e.g. 3D scanners, depth scanners) are used (in alternative or in addition) to create a 3D rendering. The 3D rendering can be shown on a 2D display, in virtual reality, in augmented reality, or as holographic image, or a combination thereof.

The synthesized bot is able to say anything or do anything. However, the synthesized bots are configured by the persona libraries to say and do things that are relevant or characteristic to the given person on which they are based upon, so that is appears as if the synthesized bot is controlled by the given person or is actually the given person.

Figure 21:
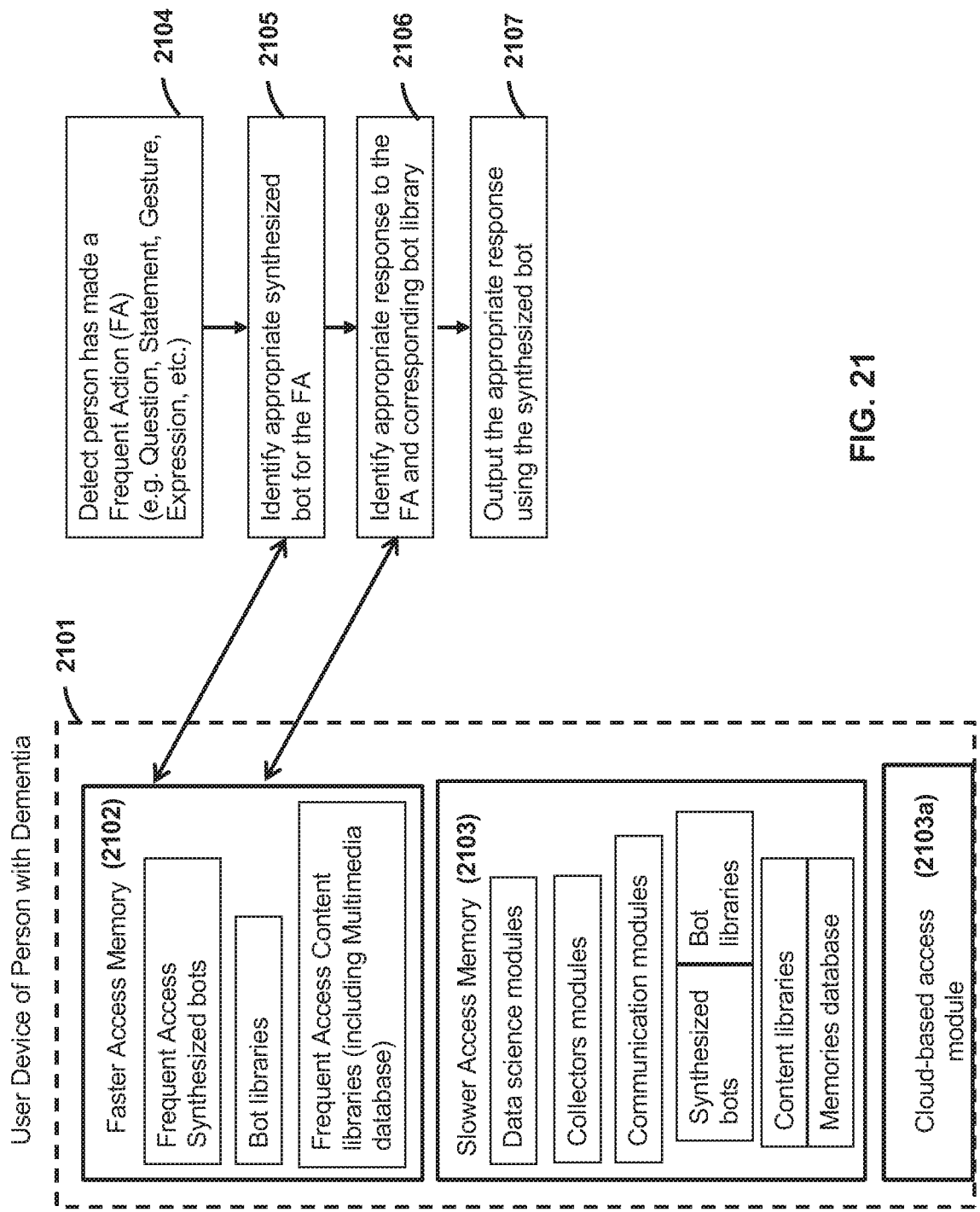
FIGS. 21 to 24 are flow diagrams of example executable instructions for a smart device interacting with a person with dementia using a synthesized bot of a contact who has dementia.

FIG. 21 shows an example of a user device 2101 who has dementia. For example, this is similar to the device 1501 in FIG. 15. In FIG. 21, the faster access memory include frequent access synthesized bots and bot libraries. For example, there is frequently accessed synthesized bot for a daughter and a frequently accessed synthesized bot for a wife of the father with dementia. The slower access memory 2103 also includes other synthesized bots and corresponding bot libraries (e.g. a synthesized doctor bot and related libraries, a synthesized bot of the father's friend and related libraries, etc.). There is also a cloud-based access module 2103*a*.

At block 2104: the user device detects that the person with dementia has made a Frequent Action (FA) (e.g. Question, Statement, Gesture, Expression, etc.). At block 2105: the user device identifies the appropriate synthesized bot for the FA, by accessing the faster access memory. At block 2106: the user device identifies the appropriate response to the FA and corresponding bot library. At block 2107: the user device outputs the appropriate response using the synthesized bot. For example, the father with dementia refers to his daughter as "Lulu", a nick name only associated with the daughter when she was a young girl. The father, for example, says: "When is Lulu going to walk the dog?" Therefore, the synthesized bot is of the father's daughter as a young girl. The synthesized bot of the daughter as a young girl accesses images of the family's old pet that they owned when Lulu was a girl. The response could include an oral response from the synthesized bot (e.g. the Lulu as a young girl): "I already walked our dog". The response could also be followed by a video from that same time frame of the family dog.

Figure 22:
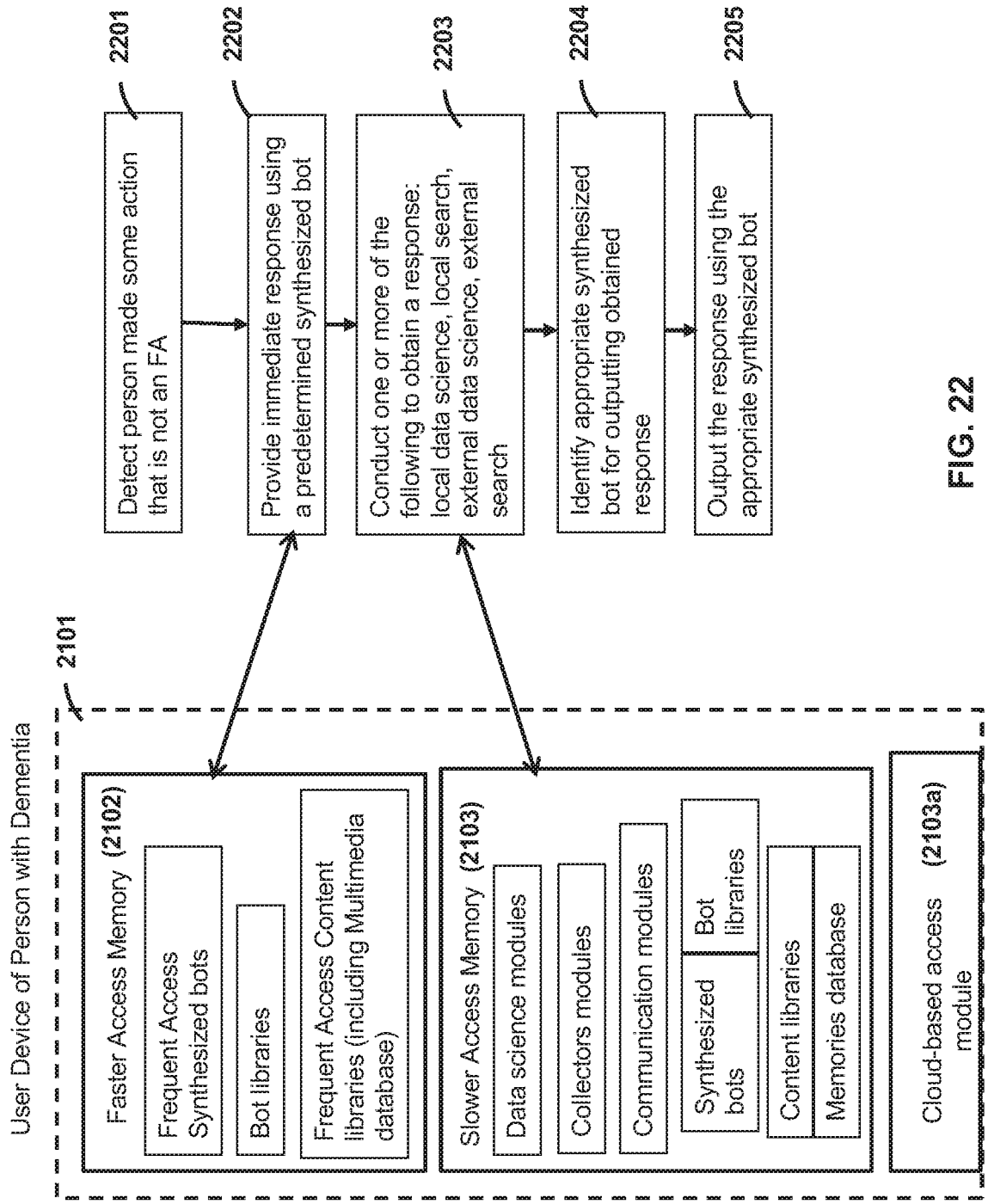

Turning to FIG. 22, the user device executes instructions to: detect the person made some action that is not an FA (block 2201); provide an immediate response using a pre-determined synthesized bot (block 2202); conducts one or more of the following to obtain a response: local data science, local search, external data science, external search (block 2203); identify an appropriate synthesized bot for outputting obtained response by accessing the slower access memory (block 2204); and output the response using the appropriate synthesized boy (block 2205).

At block 2202, this pre-determined bot is like an administrative or secretarial bot. It may be a synthesized bot of someone familiar to the person with dementia, or not.

Figure 23:
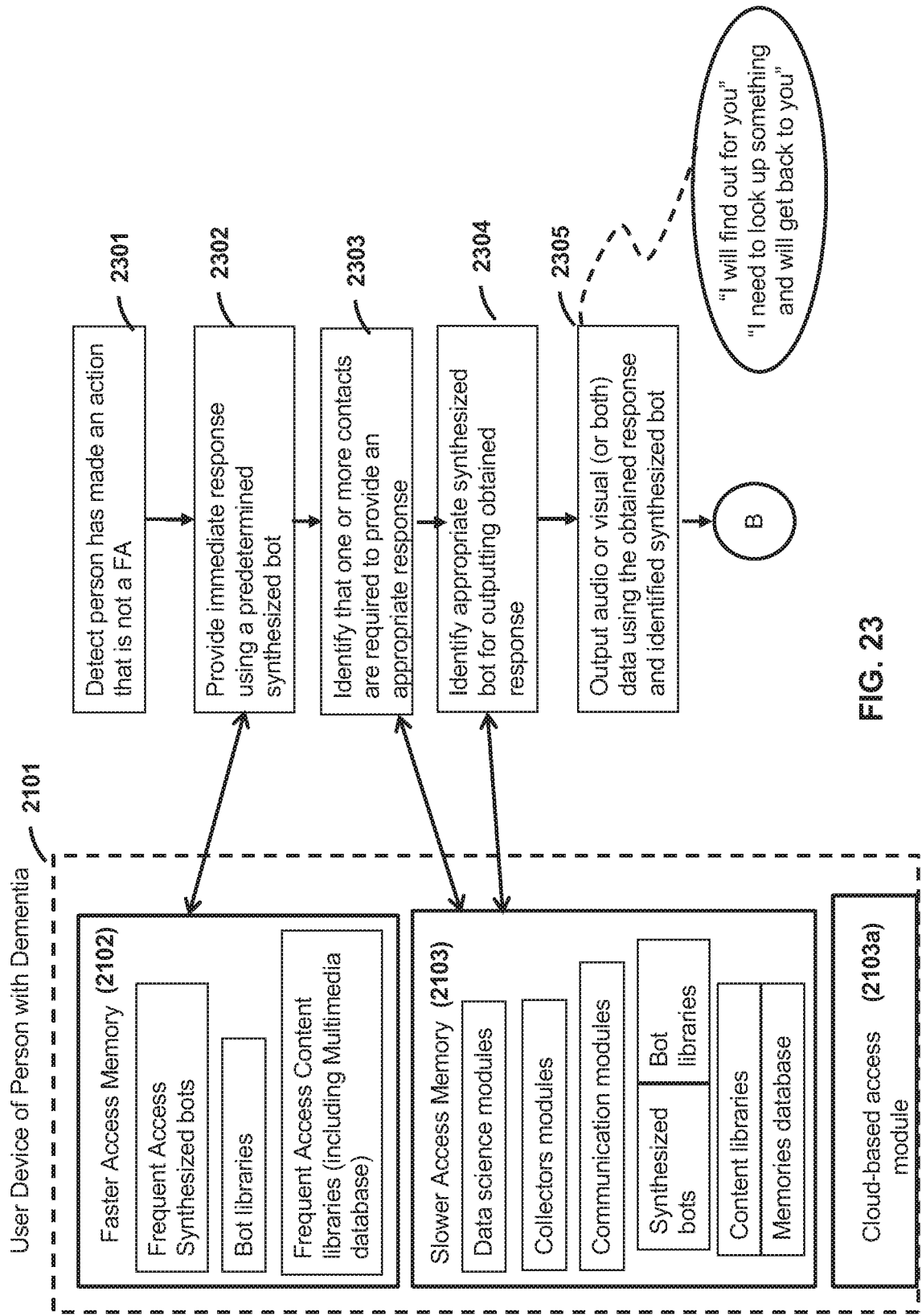
Figure 24:
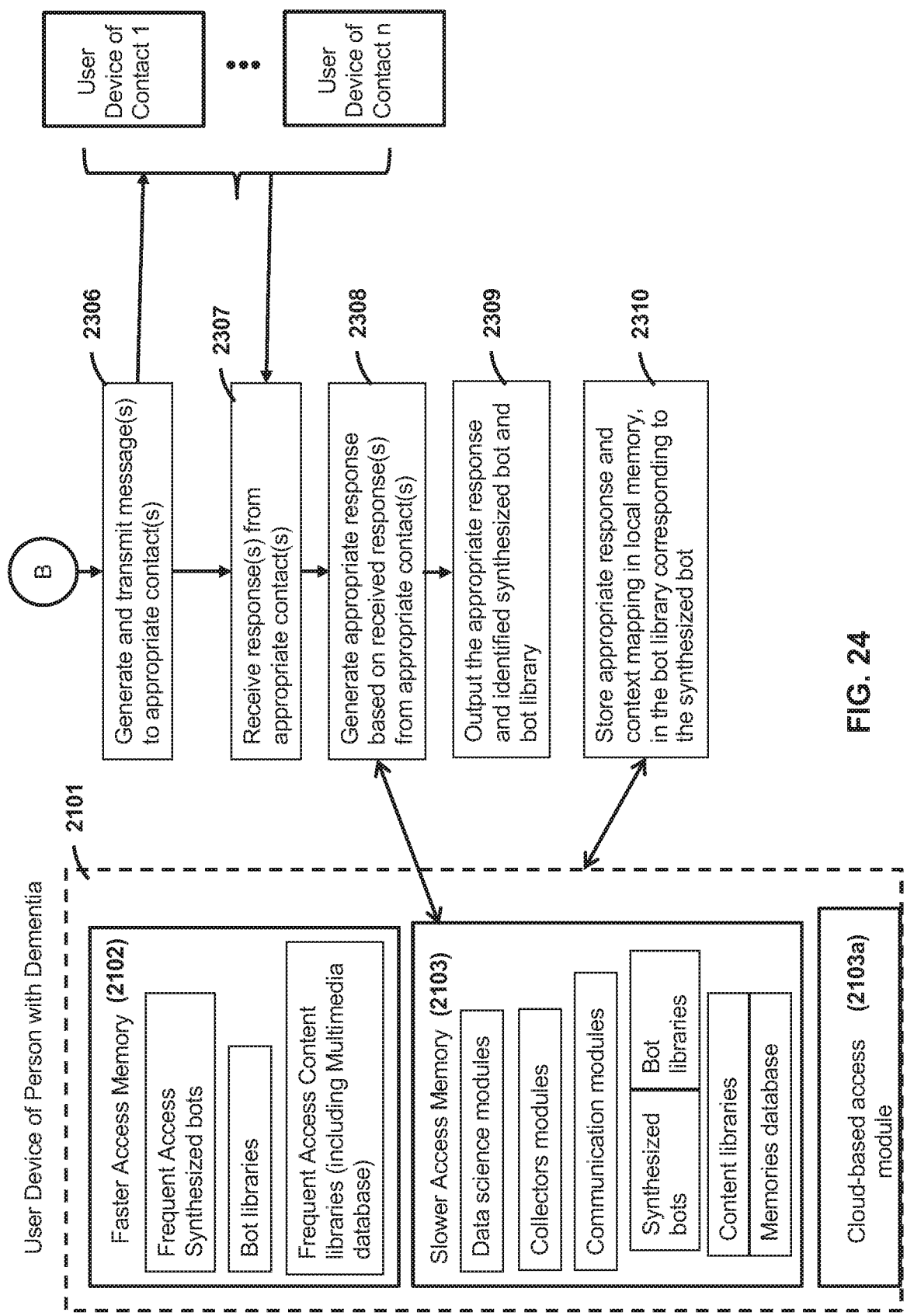

FIGS. 23 and 24 are similar to the operations in FIGS. 17 and 18. However, the operations are more general to the synthesized bots. The following operations are performed by the user device 2101.

Block 2301: Detect person has made an action that is not a FA.

Block 2302: Provide immediate response using a predetermined synthesized bot Block 2303: Identify that one or more contacts are required to provide an appropriate response.

Block 2304: Identify appropriate synthesized bot for outputting obtained response.

Block 2305: Output audio or visual (or both) data using the obtained response and identified synthesized bot.

Block 2306: Generate and transmit message(s) to appropriate contact(s).

Block 2307: Receive response(s) from appropriate contact(s).

Block 2308: Generate appropriate response based on received response(s) from appropriate contact(s).

Block 2309: Output the appropriate response and identified synthesized bot and bot library.

Block 2310: Store appropriate response and context mapping in local memory, in the bot library corresponding to the synthesized bot.

Figure 25A:
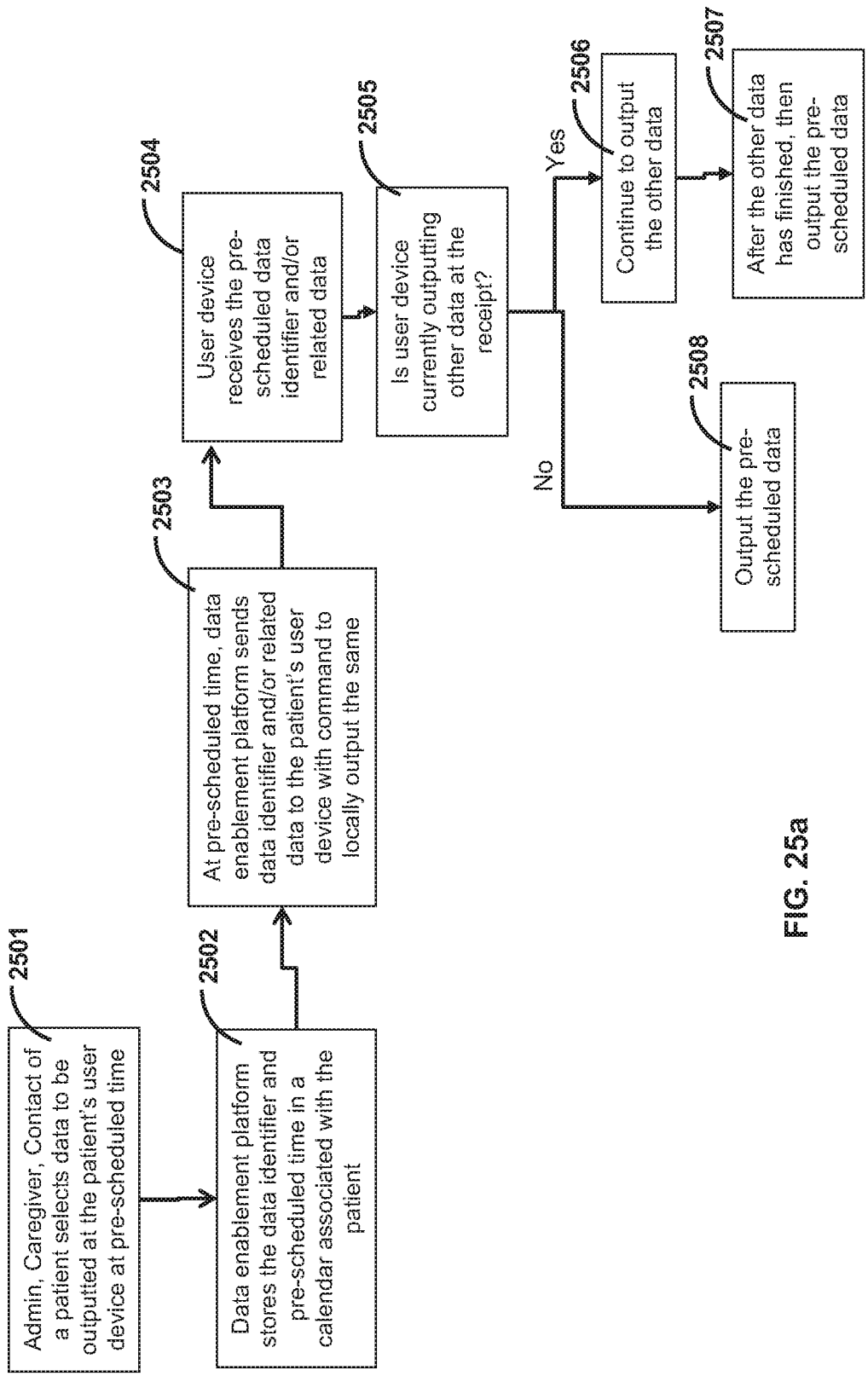
FIGS. 25a and 25b are flow diagrams of example executable instructions for a data enablement platform interacting with a user device to output data to a person with dementia at a pre-scheduled time.

Turning to FIG. 25a, an example embodiment is shown for outputting data at a user device at pre-scheduled times.

Block 2501: Administrator, Caregiver, or Contact of a patient selects data to be outputted at the patient's user device at pre-scheduled time.

Block 2502: Data enablement platform stores the data identifier and pre-scheduled time in a calendar associated with the patient.

Block 2503: At a pre-scheduled time, the data enablement platform sends a data identifier and/or related data to the patient's user device with a command to locally output the same.

Block 2504: User device receives the pre-scheduled data identifier and/or related data Block 2505: User device determines if it is currently outputting other data at the receipt of the command to play the pre-scheduled data?

Block 2506: If so, then the user device continues to output the other data. For example, the user device is in the middle of playing a song or playing a video.

Block 2507: After the other data has finished, then the user device outputs the pre-scheduled data.

Block 2508: If the user device is not currently outputting other data, then it outputs the pre-scheduled data.

Figure 25B:
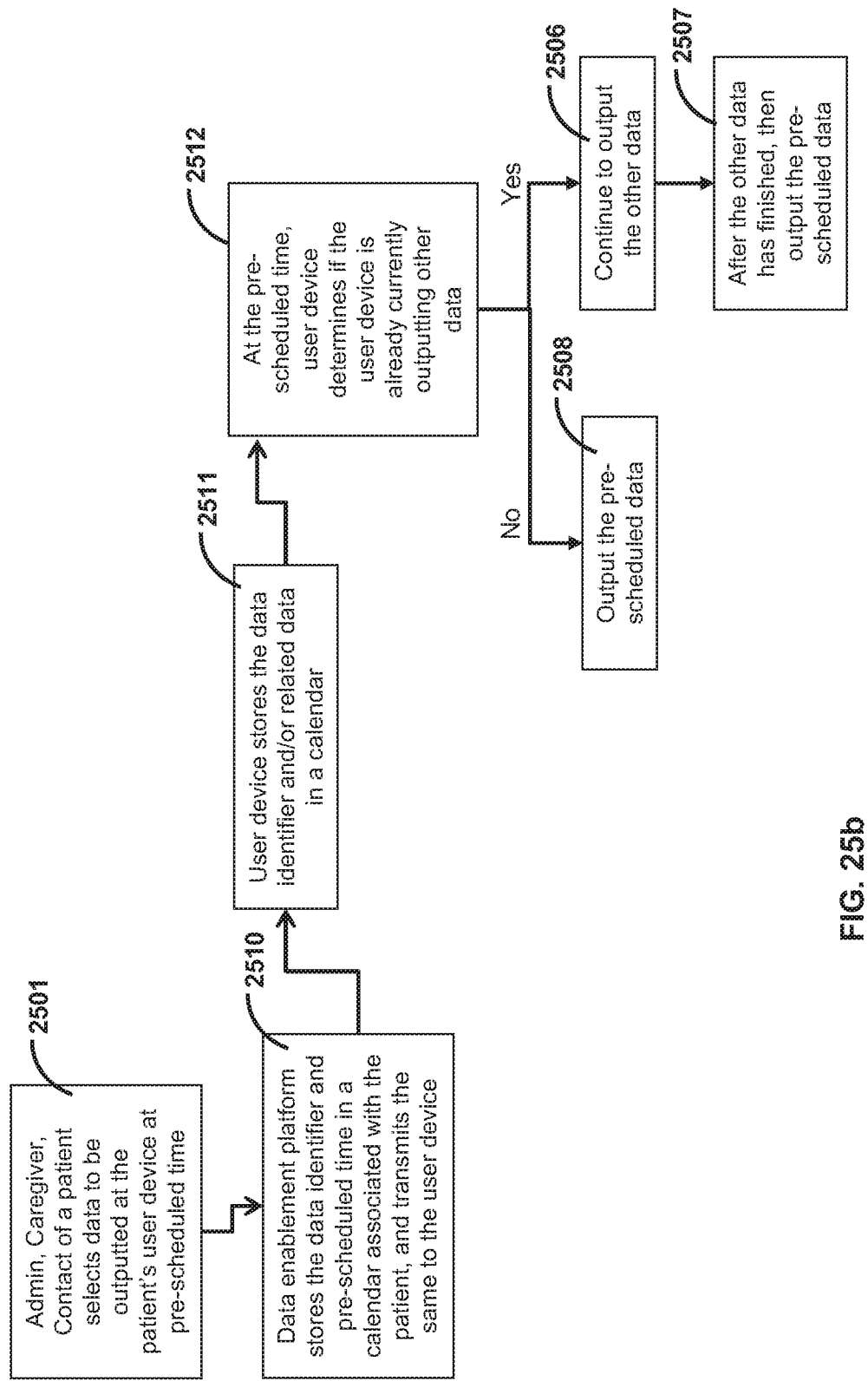

FIG. 25b is similar to FIG. 25a, with some difference. After block 2501, the data enablement platform stores the data identifier and pre-scheduled time in a calendar associated with the patient, and then transmits the same to the user device (block 2510). The user device stores the data identifier and/or related data in a calendar (block 2511). At the pre-scheduled time, user device determines if the user device is already currently outputting other data (block 2512). Blocks 2506, 2507, or 2508 are then executed.

Other example features of the devices, systems and the methods are provided below.

Additional general example embodiment and aspects are described below.

In an example embodiment, an oral computing device is provided, which includes a housing that holds at least: a memory device that stores thereon a data enablement application that includes a conversational bot and a user account ID, the user account ID used to access private databases; a microphone that is configured to record a user's spoken words as audio data; a processor configured to use the conversational bot to identify contextual data associated with the audio data, the contextual data including a current mode of the data enablement application and the user account ID; a data communication device configured to transmit the audio data and the contextual data via a data network and, in response, receive response data, wherein the response data is a function of data obtained from the private database and data obtained from external databases; and an audio speaker that is controlled by the processor to output the response data as audio response data.

In an example aspect, the oral computing device is a wearable device to dynamically interact with the data. For example, the wearable device includes inertial measurement sensors. In another example, the wearable device is a smart watch. In another example, the wearable device is a headset. In another example, the wearable device projects images to provide augmented reality.

In another example aspect, the oral computing device projects light images on surrounding surfaces to provide augmented reality of virtual reality. In another example aspect, the oral computing device is in data connection with other devices that projects light images to provide augmented reality or virtual reality in a room. In effect, people that are physically present in the room, or virtual people being displayed by the projected light images, simultaneously interact and collaborate with each other.

In an example aspect, the oral computing device includes a graphics processing unit (GPU) that exchanges data with the processor, the GPU configured to pre-process the audio data using parallel threaded computations to extract data features, and the data communication device transmits the extracted data features in association with the contextual data and the audio data.

In an example embodiment, the oral computing device is a user device 102 or the specific embodiment of the OCD 301.

In another general example embodiment, a data enablement system (also herein called the data enablement platform) is provided that includes cloud computing servers that ingest audio data originating from one or more user devices, the audio data comprising at least oral conversation of one or more users, and the cloud computing servers configured to apply machine learning computations to extract at least content and sentiment data features. The data enablement system also includes data science servers in data communication with the cloud computing servers, internal applications and databases, and an external artificial intelligence computing platform. The data science servers also include a library of data science algorithms used to process the content and sentiment features using internal data obtained from the internal applications and databases, and external data obtained from the external artificial intelligence computing platform. The data science servers output response data to the cloud computing servers, the response data being in response to the audio data. Subsequently, the cloud computing servers format the response data into an audio data format playable by a given user device, and transmit the formatted response data.

In an example embodiment, systems, methods and devices are provided which machine learns and dynamically speaks, in real time, between a patient and a smart device(s) so that there is a normal pace conversation in the patients native tongue.

In an example embodiment, systems, methods and devices are provided that provide patients with intelligent Q&A conversation (tracking me, help me's, tell me's, show me's, assist me's) between a patient and the appropriate person. The appropriate person can be the spouse, family member, friend, doctor, or caregiver.

In an example embodiment, using the NLP and DSP voice synthesizer, the systems or device, or both, determine who is the right person to answer the patients questions and selects the correct voice library related to the person that should answer the question.

In an example embodiment, the data enablement system selects the right answer to the question and or dynamic conversational content library, synthesizes the responders voice, and then plays the answer/conversation using the appropriate person's voice.

In an example embodiment, systems, methods and devices are provided which utilize NLP to help detect the patient's dementia state by listening to oral stress patterns such as stammering, excited, happy, sad, depressed, anger, fearful, cussing, dynamic range, content, and then autonomously use these detected states to take autonomous actions such as playing the patient's favorite music, asking the patient about a family trip, etc. in order to calm the patient.

In an example embodiment, systems, methods and devices are provided which machine learn and dynamically provides more or less oral answering assistance and or physical IoT enabled assistance to the patient depending upon the current patient dementia state.

In an example embodiment, systems, methods and devices are provided which capture and machine vision learn a patients' current dementia state by comparing a baseline physical patient movement (ex. ability to walk and balance self) to an extremely slow and jittery state, to a stumble, fall, and repeat state.

In an example embodiment, systems, methods and devices are provided which machine learn the patient's internal patient data base line (brain wave, vital signs, sensor data etc.) by comparing a baseline physical movement (ex. ability to walk and balance self) to an extremely slow and jittery and unstable human motor movement state.

In an example embodiment, systems, methods and devices are provided which machine learn and dynamically provide more or less assistance physical assistance to the patient (e.g. opening door, turning on water, pressing an elevator button, turning on tv) depending upon the patient dementia state.

In an example embodiment, systems, methods and devices are provided that take both oral NLP responses along with IoT patient sensor data in order to provide sensitive conversations that are appropriate with the patient's current dementia state.

In an example embodiment, systems, methods and devices are provided that provide real time updates and recommendations to loved ones, care givers, and health professionals based on the interactions between the patient and the smart devices (vital signs, falling, no movement, singing, walking, etc.).

In an example embodiment, systems, methods and devices are provided that can solicit answers from loved ones, care givers, and health professionals and incorporate these answers into the frequently asked questions (data enablement system) that the patients ask(s).

In an example embodiment, systems, methods and devices are provided that can speak in the same voice (tone, frequency, timbre) as a loved one so that when the patient speaks to the smart device, the response is from a loved one In an example embodiment, systems, methods and devices are provided that have a library of voices so that the patient can receive frequently asked questions from multiple people (brothers, sisters, mother, father, children, care givers)

In an example embodiment, systems, methods and devices are provided that can autonomously select content from private databases, social sites, 3rd party data in order to play patient preferred audio books, music, family slides shows, videos, social sites, etc.

In another general example embodiment, a user device includes: a microphone for obtaining voice data from a first person; a processor for processing the voice data to obtain text data; and a communication device for transmitting the text data to a server system. In response, the communication system receives from the server system: first response data stored at or in relation to the server system; and a response identifier that identifies second response data provided by a third party data source. The communication device obtains the second response data from the third party data source using the response identifier. The processor combines the first response data and the second response data to generate combined response. The user device also includes one or more output devices that output the combined response.

In an example aspect, the first response data is outputted first followed by the second response data.

In another example aspect, the first response data is overlaid the second response data.

In another example aspect, the first response data is outputted after outputting the second response data.

In another example aspect, the first response data comprises audio data of a second person that is familiar to the first person.

In another example aspect, the first response data comprises audio data and visual data that are of a second person that is familiar to the first person.

In another example aspect, the second response data includes at least one of a video, an image, and audio data.

In another example aspect, the one or more output devices comprise a multimedia projector.

In another example aspect, the one or more output devices comprise a holographic projector.

In another example aspect, the user device further includes memory that stores one or more synthesized bots of one or more people that are familiar to the first user, and libraries specific to each of the one or more synthesized bots.

In another example aspect, a given synthesized bot is voice bot has a synthesized voice corresponding to given person that is familiar to the first user.

In another example aspect, a given synthesized bot includes a static image and voice data corresponding to given person that is familiar to the first user.

In another example aspect, a given synthesized bot includes a synthesized moving image and voice data corresponding to given person that is familiar to the first user.

In another example aspect, a given synthesized bot includes a synthesized moving 3D rendering and voice data corresponding to given person that is familiar to the first user.

In another example aspect, a given synthesized bot has related given libraries corresponding to a given person that is familiar to the first user, and the given libraries include persona data of the given person that are mapped to different contexts.

In another example aspect, the different contexts are different time frames of the given person's life.

In another example aspect, the different contexts are different locations associated with the given person.

In another example aspect, the different contexts are different topics associated with the given person.

In another example aspect, the memory comprises a first memory and a second memory, the first memory having faster access speed compared to the second memory; and a first synthesized bot is stored in the first memory and a second synthesized bot is stored in the second memory.

In another general example embodiment, a data enablement platform includes one or more servers that receive user data; match the user data to pre-stored data to search for a response identifier of a 3rd party data source and internal response data; and transmit both the response identifier and the internal response data with executable instructions to later combine the internal response data with 3rd party response data obtained via the response identifier.

In an example aspect, the user data matches the pre-stored data according to a certain percentage threshold.

In another example aspect, the user data is text data outputted by a speech-to-text computing process.

In another example aspect, the executable instructions initiate a user device to output the internal response data first and then the 3rd party response data.

In another example aspect, the data enablement platform receives multiple communications of user data over time to build a behavior model of a given user.

In another example aspect, the behavior model of the given user is used to identify patterns in the given user's behavior.

In another example aspect, the user data includes body posture data.

In another example aspect, the user data includes facial expression data.

In another example aspect, the user data includes voice data.

In another example aspect, the user data is from a first user, and the one or more server comprise memory that has stored thereon a synthesized bot corresponding to a second person that is familiar to the first user.

In another example aspect, the synthesized bot is a voice bot of the second person.

In another example aspect, the synthesized bot includes a static image and voice data corresponding to the second person.

In another example aspect, the synthesized bot includes a synthesized moving image and voice data corresponding to the second person.

In another example aspect, the synthesized bot includes a synthesized moving 3D rendering and voice data corresponding to the second person.

In another example aspect, user data is language data in a first language, and the one or more servers translate the language data to a second language, and transmit the translated language data to a user device.

In another example aspect, the one or more servers further transmit a command to an IoT device based upon the received user data.

In another example aspect, the user data is a certain set of words associated with a first user, and if the certain set of words has been detected a certain number of times within a certain time frame, then the one or more servers transmit a notification message to a second user.

It will be appreciated that any module or component exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the servers or computing devices or accessible or connectable thereto. Any application or module herein described may be implemented using computer readable/executable instructions that may be stored or otherwise held by such computer readable media.

It will be appreciated that different features of the example embodiments of the system and methods, as described herein, may be combined with each other in different ways. In other words, different devices, modules, operations, functionality and components may be used together according to other example embodiments, although not specifically stated.

The steps or operations in the flow diagrams described herein are just for example. There may be many variations to these steps or operations according to the principles described herein. For instance, the steps may be performed in a differing order, or steps may be added, deleted, or modified.

It will also be appreciated that the examples and corresponding system diagrams used herein are for illustrative purposes only. Different configurations and terminology can be used without departing from the principles expressed herein. For instance, components and modules can be added, deleted, modified, or arranged with differing connections without departing from these principles.

Although the above has been described with reference to certain specific embodiments, various modifications thereof will be apparent to those skilled in the art without departing from the scope of the claims appended hereto.

The invention claimed is:

1. A user device comprising:
a microphone for obtaining voice data from a first person;
a processor for processing the voice data to obtain text data;
a communication device for transmitting the text data to a server system and, in response, receive from the server system:
first response data stored at or in relation to the server system; and
a response identifier that identifies second response data provided by a third party data source;
the communication device obtaining the second response data from the third party data source using the response identifier;
the processor combining the first response data and the second response data to generate combined response;
one or more output devices that output the combined response; and
memory that stores one or more synthesized bots of one or more people that are familiar to the first user, and one or more libraries specific to each of the one or more synthesized bots.

2. The user device of claim 1 wherein the first response data is outputted first followed by the second response data.

3. The user device of claim 1 wherein the first response data is overlaid the second response data.

4. The user device of claim 1 wherein the first response data is outputted after outputting the second response data.

5. The user device of claim 1 wherein the first response data comprises audio data of a second person that is familiar to the first person.

6. The user device of claim 1 wherein the first response data comprises audio data and visual data that are of a second person that is familiar to the first person.

7. The user device of claim 1 wherein the second response data includes at least one of a video, an image, and audio data.

8. The user device of claim 1 wherein a given synthesized bot comprises a synthesized voice corresponding to a given person that is familiar to the first user.

9. The user device of claim 1 wherein a given synthesized bot comprises an image and voice data corresponding to a given person that is familiar to the first user.

10. The user device of claim 1 wherein a given synthesized bot has related given libraries corresponding to a given person that is familiar to the first user, and the given libraries include personal data of the given person that are mapped to different contexts.

11. The user device of claim 10 wherein the different contexts comprise different time frames of the given person's life.

12. The user device of claim 10 wherein the different contexts comprise different locations associated with the given person.

13. The user device of claim 10 wherein the different contexts comprise different topics associated with the given person.

14. A data enablement platform comprising: one or more servers that are configured to at least receive user data of a first user, the user data transmittable by a user device; the one or more servers comprising memory that has stored thereon a synthesized bot corresponding to a second person that is familiar to the first user; the one or more servers further configured to at least match the user data to pre-stored data to search for a response identifier of a 3rd party data source and internal response data, wherein the one or more servers of the data enablement platform are in data communication with the $3^{rd}$ party data source; and the one or more servers are further configured to at least transmit a response comprising the response identifier, the internal response data, and executable instructions that combine the internal response data with 3rd party response data obtained via the response identifier, wherein the response is transmittable to the user device.

15. The data enablement platform of claim 14 wherein the user data matches the pre-stored data according to a certain percentage threshold.

16. The data enablement platform of claim 14 wherein the user data is text data outputted by a speech-to-text computing process.

17. The data enablement platform of claim 14 wherein the executable instructions are configured to initiate the user device to output the internal response data first and then the 3rd party response data.

18. The data enablement platform of claim 14 receiving multiple communications of user data over time to build a behavior model of a given user.

19. The data enablement platform of claim 14 wherein the user data comprises body posture data.

20. The data enablement platform of claim 14 wherein the user data comprises facial expression data.

21. The data enablement platform of claim 14 wherein the user data comprises at least one of text data and voice data.

22. The data enablement platform of claim 14 wherein the synthesized bot is a voice bot of the second person.

23. The data enablement platform of claim 14 wherein the synthesized bot includes an image and voice data corresponding to the second person.

24. The data enablement platform of claim 14 wherein the user data comprises language data in a first language, and the one or more servers translate the language data to a second language, and the response further comprises the translated language data.

25. The data enablement platform of claim 14 wherein the one or more servers further transmit a command to an IoT device based upon the user data.

26. The data enablement platform of claim 14, wherein the user data is a certain set of words associated with the first user, and if the certain set of words has been detected a certain number of times within a certain time frame, then the one or more servers transmit a notification message, the notification message transmittable to a second user device.

* * * * *